(12) United States Patent
Mickelsen et al.

(10) Patent No.: US 10,624,693 B2
(45) Date of Patent: Apr. 21, 2020

(54) METHOD AND APPARATUS FOR RAPID AND SELECTIVE TISSUE ABLATION WITH COOLING

(71) Applicant: Farapulse, Inc., Menlo Park, CA (US)

(72) Inventors: Steven R. Mickelsen, Iowa City, IA (US); Raju Viswanathan, Mountain View, CA (US); Allan Zingeler, Menlo Park, CA (US)

(73) Assignee: Farapulse, Inc., Menlo Park, CA (US)

( * ) Notice: Subject to any disclaimer, the term of this patent is extended or adjusted under 35 U.S.C. 154(b) by 304 days.

(21) Appl. No.: 15/354,475

(22) Filed: Nov. 17, 2016

(65) Prior Publication Data

US 2017/0065330 A1 Mar. 9, 2017

Related U.S. Application Data

(63) Continuation of application No. PCT/US2015/035582, filed on Jun. 12, 2015.
(Continued)

(51) Int. Cl.
*A61B 18/14* (2006.01)
*A61B 17/08* (2006.01)
(Continued)

(52) U.S. Cl.
CPC .............. *A61B 18/14* (2013.01); *A61B 17/08* (2013.01); *A61B 18/1442* (2013.01);
(Continued)

(58) Field of Classification Search
CPC ..... A61B 17/08; A61B 18/14; A61B 18/1442; A61B 2018/00005; A61B 2018/00613;
(Continued)

(56) References Cited

U.S. PATENT DOCUMENTS

| 4,200,104 A | 4/1980 | Harris |
| 4,470,407 A | 9/1984 | Hussein |

(Continued)

FOREIGN PATENT DOCUMENTS

| EP | 1042990 A1 | 10/2000 |
| EP | 1125549 | 8/2001 |

(Continued)

OTHER PUBLICATIONS

Partial Supplementary European Search Report for European Application No. 13827672.0, dated Mar. 23, 2016, 6 pages.
(Continued)

*Primary Examiner* — Michael F Peffley
(74) *Attorney, Agent, or Firm* — Cooley LLP

(57) ABSTRACT

Systems, tools and methods are disclosed for the selective and rapid application of DC voltage to drive irreversible electroporation, with the system controller capable of being configured to apply voltages to independently selected subsets of electrodes and capable of generating at least one control signal to maintain the temperature near an electrode head within a desired range of values. Electrode clamp devices are also disclosed for generating electric fields to drive irreversible electroporation while modulating temperature to elevate the irreversible electroporation threshold utilizing a variety of means such as cooling fluid or solid state thermoelectric heat pumps.

20 Claims, 15 Drawing Sheets

Related U.S. Application Data

(60) Provisional application No. 61/997,869, filed on Jun. 12, 2014.

(51) Int. Cl.
*A61B 18/00* (2006.01)
*A61B 90/00* (2016.01)

(52) U.S. Cl.
CPC .............. *A61B 2018/00005* (2013.01); *A61B 2018/00613* (2013.01); *A61B 2018/00779* (2013.01); *A61B 2018/00791* (2013.01); *A61B 2090/061* (2016.02)

(58) Field of Classification Search
CPC ........... A61B 2018/00779; A61B 2018/00791; A61B 2090/061
See application file for complete search history.

(56) References Cited

U.S. PATENT DOCUMENTS

| | | |
|---|---|---|
| 4,739,759 A | 4/1988 | Rexroth et al. |
| 5,234,004 A | 8/1993 | Hascoet et al. |
| 5,242,441 A | 9/1993 | Avitall |
| 5,257,635 A | 11/1993 | Langberg |
| 5,281,213 A | 1/1994 | Milder et al. |
| 5,304,214 A | 4/1994 | DeFord et al. |
| 5,306,296 A | 4/1994 | Wright et al. |
| 5,334,193 A | 8/1994 | Nardella |
| 5,341,807 A | 8/1994 | Nardella |
| 5,342,301 A | 8/1994 | Saab |
| 5,398,683 A | 3/1995 | Edwards et al. |
| 5,443,463 A | 8/1995 | Stern et al. |
| 5,454,370 A | 10/1995 | Avitall |
| 5,515,848 A | 5/1996 | Corbett, III et al. |
| 5,531,685 A | 7/1996 | Hemmer et al. |
| 5,545,161 A | 8/1996 | Imran |
| 5,578,040 A | 11/1996 | Smith |
| 5,617,854 A | 4/1997 | Munsif |
| 5,624,430 A | 4/1997 | Eton et al. |
| 5,667,491 A | 9/1997 | Pliquett et al. |
| 5,672,170 A | 9/1997 | Cho |
| 5,700,243 A | 12/1997 | Narciso, Jr. |
| 5,702,438 A | 12/1997 | Avitall |
| 5,706,823 A | 1/1998 | Wodlinger |
| 5,722,400 A | 3/1998 | Ockuly et al. |
| 5,722,402 A | 3/1998 | Swanson et al. |
| 5,749,914 A | 5/1998 | Janssen |
| 5,779,699 A | 7/1998 | Lipson |
| 5,788,692 A | 8/1998 | Campbell et al. |
| 5,810,762 A | 9/1998 | Hofmann |
| 5,833,710 A | 11/1998 | Jacobson |
| 5,836,874 A | 11/1998 | Swanson et al. |
| 5,836,942 A | 11/1998 | Netherly et al. |
| 5,836,947 A | 11/1998 | Fleischman et al. |
| 5,843,154 A | 12/1998 | Osypka |
| 5,849,028 A | 12/1998 | Chen |
| 5,863,291 A | 1/1999 | Schaer |
| 5,868,736 A | 2/1999 | Swanson et al. |
| 5,871,523 A | 2/1999 | Fleischman et al. |
| 5,876,336 A | 3/1999 | Swanson et al. |
| 5,885,278 A | 3/1999 | Fleischman et al. |
| 5,895,404 A | 4/1999 | Ruiz |
| 5,899,917 A | 5/1999 | Edwards et al. |
| 5,904,709 A | 5/1999 | Arndt et al. |
| 5,916,158 A | 6/1999 | Webster, Jr. |
| 5,916,213 A | 6/1999 | Haissaguerre et al. |
| 5,921,924 A | 7/1999 | Avitall |
| 5,928,269 A | 7/1999 | Alt |
| 5,928,270 A | 7/1999 | Ramsey, III |
| 6,002,955 A | 12/1999 | Willems et al. |
| 6,006,131 A | 12/1999 | Cooper et al. |
| 6,009,351 A | 12/1999 | Flachman |
| 6,014,579 A | 1/2000 | Pomeranz et al. |
| 6,029,671 A | 2/2000 | Stevens et al. |
| 6,033,403 A | 3/2000 | Tu et al. |
| 6,035,238 A * | 3/2000 | Ingle .................. A61B 18/1485 607/101 |
| 6,045,550 A | 4/2000 | Simpson et al. |
| 6,068,653 A | 5/2000 | LaFontaine |
| 6,071,274 A | 6/2000 | Thompson et al. |
| 6,071,281 A | 6/2000 | Burnside et al. |
| 6,074,389 A * | 6/2000 | Levine .............. A61B 18/1402 606/45 |
| 6,076,012 A | 6/2000 | Swanson et al. |
| 6,090,104 A | 7/2000 | Webster, Jr. |
| 6,096,036 A | 8/2000 | Bowe et al. |
| 6,113,595 A | 9/2000 | Muntermann |
| 6,119,041 A | 9/2000 | Pomeranz et al. |
| 6,120,500 A | 9/2000 | Bednarek et al. |
| 6,146,381 A | 11/2000 | Bowe et al. |
| 6,164,283 A | 12/2000 | Lesh |
| 6,167,291 A | 12/2000 | Barajas et al. |
| 6,171,305 B1 | 1/2001 | Sherman |
| 6,216,034 B1 | 4/2001 | Hofmann et al. |
| 6,219,582 B1 | 4/2001 | Hofstad et al. |
| 6,223,085 B1 | 4/2001 | Dann et al. |
| 6,231,518 B1 | 5/2001 | Grabek et al. |
| 6,245,064 B1 | 6/2001 | Lesh et al. |
| 6,251,107 B1 | 6/2001 | Schaer |
| 6,251,128 B1 | 6/2001 | Knopp et al. |
| 6,270,476 B1 | 8/2001 | Santoianni et al. |
| 6,272,384 B1 | 8/2001 | Simon et al. |
| 6,287,306 B1 | 9/2001 | Kroll et al. |
| 6,314,963 B1 | 11/2001 | Vaska et al. |
| 6,322,559 B1 | 11/2001 | Daulton et al. |
| 6,350,263 B1 | 2/2002 | Wetzig et al. |
| 6,370,412 B1 | 4/2002 | Armoundas et al. |
| 6,391,024 B1 | 5/2002 | Sun et al. |
| 6,447,505 B2 | 9/2002 | McGovern et al. |
| 6,464,699 B1 | 10/2002 | Swanson |
| 6,470,211 B1 | 10/2002 | Ideker et al. |
| 6,502,576 B1 | 1/2003 | Lesh |
| 6,503,247 B2 | 1/2003 | Swartz et al. |
| 6,517,534 B1 | 2/2003 | McGovern et al. |
| 6,527,724 B1 | 3/2003 | Fenici |
| 6,527,767 B2 | 3/2003 | Wang et al. |
| 6,592,581 B2 | 7/2003 | Bowe |
| 6,595,991 B2 | 7/2003 | Tollner et al. |
| 6,607,520 B2 | 8/2003 | Keane |
| 6,623,480 B1 | 9/2003 | Kuo et al. |
| 6,638,278 B2 | 10/2003 | Falwell et al. |
| 6,666,863 B2 | 12/2003 | Wentzel et al. |
| 6,669,693 B2 | 12/2003 | Friedman |
| 6,702,811 B2 | 3/2004 | Stewart et al. |
| 6,719,756 B1 | 4/2004 | Muntermann |
| 6,723,092 B2 | 4/2004 | Brown et al. |
| 6,728,563 B2 | 4/2004 | Rashidi |
| 6,743,225 B2 | 6/2004 | Sanchez et al. |
| 6,743,226 B2 | 6/2004 | Cosman et al. |
| 6,743,239 B1 | 6/2004 | Kuehn et al. |
| 6,764,486 B2 | 7/2004 | Natale |
| 6,780,181 B2 | 8/2004 | Kroll et al. |
| 6,805,128 B1 | 10/2004 | Pless |
| 6,807,447 B2 | 10/2004 | Griffin, III |
| 6,892,091 B1 | 5/2005 | Ben-Haim et al. |
| 6,893,438 B2 | 5/2005 | Hall et al. |
| 6,926,714 B1 | 8/2005 | Sra |
| 6,955,173 B2 | 10/2005 | Lesh |
| 6,960,206 B2 | 11/2005 | Keane |
| 6,960,207 B2 | 11/2005 | Vanney et al. |
| 6,972,016 B2 | 12/2005 | Hill |
| 6,973,339 B2 | 12/2005 | Govari |
| 6,979,331 B2 | 12/2005 | Hintringer et al. |
| 6,984,232 B2 | 1/2006 | Vanney et al. |
| 6,985,776 B2 | 1/2006 | Kane et al. |
| 7,001,383 B2 | 2/2006 | Keidar |
| 7,041,095 B2 | 5/2006 | Wang et al. |
| 7,113,831 B2 * | 9/2006 | Hooven .............. A61B 18/1445 606/41 |
| 7,171,263 B2 | 1/2007 | Darvish et al. |
| 7,182,725 B2 | 2/2007 | Bonan et al. |
| 7,195,628 B2 | 3/2007 | Falkenberg |
| 7,207,988 B2 | 4/2007 | Leckrone et al. |

(56) References Cited

U.S. PATENT DOCUMENTS

| | | | |
|---|---|---|---|
| 7,207,989 B2 | 4/2007 | Pike, Jr. et al. |
| 7,229,402 B2 | 6/2007 | Diaz et al. |
| 7,229,437 B2 | 6/2007 | Johnson et al. |
| 7,250,049 B2 | 7/2007 | Roop et al. |
| 7,285,116 B2 | 10/2007 | de la Rama et al. |
| 7,285,119 B2 | 10/2007 | Stewart et al. |
| 7,326,208 B2 | 2/2008 | Vanney et al. |
| 7,346,379 B2 | 3/2008 | Eng et al. |
| 7,367,974 B2 | 5/2008 | Haemmerich et al. |
| 7,374,567 B2 | 5/2008 | Heuser |
| 7,387,629 B2 | 6/2008 | Vanney et al. |
| 7,387,630 B2 | 6/2008 | Mest |
| 7,387,636 B2 | 6/2008 | Cohn et al. |
| 7,416,552 B2 | 8/2008 | Paul et al. |
| 7,419,477 B2 | 9/2008 | Simpson et al. |
| 7,419,489 B2 | 9/2008 | Vanney et al. |
| 7,422,591 B2 * | 9/2008 | Phan ............ A61B 18/14 606/49 |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,678,108 B2 | 3/2010 | Chrisitian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,850,642 B2 | 12/2010 | Moll et al. |
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stahler et al. |
| 8,133,220 B2 | 3/2012 | Lee et al. |
| 8,137,342 B2 | 3/2012 | Crossman |
| 8,145,289 B2 | 3/2012 | Calabro' et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harlev et al. |
| 8,449,535 B2 | 5/2013 | Deno et al. |
| 8,454,594 B2 | 6/2013 | Demarais et al. |
| 8,463,368 B2 | 6/2013 | Harlev et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,571,635 B2 | 10/2013 | McGee |
| 8,571,647 B2 | 10/2013 | Harlev et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 * | 2/2014 | Chornenky ............ A61B 18/14 606/32 |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,808,281 B2 | 8/2014 | Emons et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,880,195 B2 | 11/2014 | Azure |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,375,268 B2 | 6/2016 | Long |
| 9,414,881 B2 | 8/2016 | Callas et al. |
| 9,468,495 B2 | 10/2016 | Kunis et al. |
| 9,474,486 B2 | 10/2016 | Eliason et al. |
| 9,474,574 B2 | 10/2016 | Ibrahim et al. |
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |
| 9,492,228 B2 | 11/2016 | Lopes et al. |
| 9,517,103 B2 | 12/2016 | Panescu et al. |
| 9,526,573 B2 | 12/2016 | Lopes et al. |
| 9,532,831 B2 | 1/2017 | Reinders et al. |
| 9,539,010 B2 | 1/2017 | Gagner et al. |
| 9,554,848 B2 | 1/2017 | Stewart et al. |
| 9,554,851 B2 | 1/2017 | Sklar et al. |
| 9,700,368 B2 | 7/2017 | Callas et al. |
| 9,724,170 B2 | 8/2017 | Mickelsen |
| 9,757,193 B2 | 9/2017 | Zarins et al. |
| 9,782,099 B2 | 10/2017 | Williams et al. |
| 9,795,442 B2 | 10/2017 | Salahieh et al. |

(56) References Cited

U.S. PATENT DOCUMENTS

| | | |
|---|---|---|
| 9,861,802 B2 | 1/2018 | Mickelsen |
| 9,913,685 B2 | 3/2018 | Clark et al. |
| 9,931,487 B2 | 4/2018 | Quinn et al. |
| 9,987,081 B1 | 6/2018 | Bowers et al. |
| 9,999,465 B2 | 6/2018 | Long et al. |
| 10,016,232 B1 | 7/2018 | Bowers et al. |
| 10,130,423 B1 | 11/2018 | Viswanathan et al. |
| 10,172,673 B2 | 1/2019 | Viswanathan et al. |
| 10,322,286 B2 | 6/2019 | Viswanathan et al. |
| 10,433,906 B2 | 10/2019 | Mickelsen |
| 10,433,908 B2 | 10/2019 | Viswanathan et al. |
| 10,507,302 B2 | 12/2019 | Leeflang et al. |
| 10,512,505 B2 | 12/2019 | Viswanathan |
| 10,512,779 B2 | 12/2019 | Viswanathan et al. |
| 10,517,672 B2 | 12/2019 | Long |
| 2001/0000791 A1 | 5/2001 | Suorsa et al. |
| 2001/0007070 A1 | 7/2001 | Stewart et al. |
| 2001/0044624 A1 | 11/2001 | Seraj et al. |
| 2002/0052602 A1 | 5/2002 | Wang et al. |
| 2002/0077627 A1 | 6/2002 | Johnson et al. |
| 2002/0087169 A1 | 7/2002 | Brock et al. |
| 2002/0091384 A1 | 7/2002 | Hooven et al. |
| 2002/0095176 A1 | 7/2002 | Liddicoat et al. |
| 2002/0111618 A1 | 8/2002 | Stewart et al. |
| 2002/0156526 A1 | 10/2002 | Hlavka et al. |
| 2002/0161323 A1 | 10/2002 | Miller et al. |
| 2002/0169445 A1 | 11/2002 | Jain et al. |
| 2002/0177765 A1 | 11/2002 | Bowe et al. |
| 2002/0183638 A1 | 12/2002 | Swanson |
| 2003/0014098 A1 | 1/2003 | Quijano et al. |
| 2003/0018374 A1 | 1/2003 | Paulos |
| 2003/0023287 A1 | 1/2003 | Edwards et al. |
| 2003/0028189 A1 | 2/2003 | Woloszko et al. |
| 2003/0050637 A1 | 3/2003 | Maguire et al. |
| 2003/0114849 A1 | 6/2003 | Ryan |
| 2003/0125729 A1 | 7/2003 | Hooven et al. |
| 2003/0130598 A1 | 7/2003 | Manning et al. |
| 2003/0130711 A1 | 7/2003 | Pearson et al. |
| 2003/0204161 A1 | 10/2003 | Ferek Petric |
| 2003/0229379 A1 | 12/2003 | Ramsey |
| 2004/0039382 A1 | 2/2004 | Kroll et al. |
| 2004/0049181 A1 | 3/2004 | Stewart et al. |
| 2004/0049182 A1 | 3/2004 | Koblish et al. |
| 2004/0082859 A1 | 4/2004 | Schaer |
| 2004/0082948 A1 | 4/2004 | Stewart et al. |
| 2004/0087939 A1 | 5/2004 | Eggers et al. |
| 2004/0111087 A1 | 6/2004 | Stern et al. |
| 2004/0199157 A1 | 10/2004 | Palanker et al. |
| 2004/0215139 A1 | 10/2004 | Cohen |
| 2004/0231683 A1 | 11/2004 | Eng et al. |
| 2004/0236360 A1 | 11/2004 | Cohn et al. |
| 2004/0254607 A1 | 12/2004 | Wittenberger et al. |
| 2004/0267337 A1 | 12/2004 | Hayzelden |
| 2005/0033282 A1 | 2/2005 | Hooven |
| 2005/0187545 A1 | 8/2005 | Hooven et al. |
| 2005/0222632 A1 | 10/2005 | Obino |
| 2005/0251130 A1 | 11/2005 | Boveja et al. |
| 2005/0261672 A1 | 11/2005 | Deem et al. |
| 2006/0009755 A1 | 1/2006 | Sra |
| 2006/0009759 A1 | 1/2006 | Chrisitian et al. |
| 2006/0015095 A1 | 1/2006 | Desinger et al. |
| 2006/0015165 A1 | 1/2006 | Bertolero et al. |
| 2006/0024359 A1 | 2/2006 | Walker et al. |
| 2006/0058781 A1 | 3/2006 | Long |
| 2006/0111702 A1 | 5/2006 | Oral et al. |
| 2006/0142801 A1 | 6/2006 | Demarais et al. |
| 2006/0167448 A1 | 7/2006 | Kozel |
| 2006/0217703 A1 | 9/2006 | Chornenky et al. |
| 2006/0241734 A1 | 10/2006 | Marshall et al. |
| 2006/0264752 A1 | 11/2006 | Rubinsky et al. |
| 2006/0270900 A1 | 11/2006 | Chin et al. |
| 2006/0287648 A1 | 12/2006 | Schwartz |
| 2006/0293730 A1 | 12/2006 | Rubinsky et al. |
| 2006/0293731 A1 | 12/2006 | Rubinsky et al. |
| 2007/0005053 A1 | 1/2007 | Dando |
| 2007/0021744 A1 | 1/2007 | Creighton |
| 2007/0060989 A1* | 3/2007 | Deem ................ A61B 18/1477 607/99 |
| 2007/0066972 A1 | 3/2007 | Ormsby et al. |
| 2007/0129721 A1 | 6/2007 | Phan et al. |
| 2007/0129760 A1 | 6/2007 | Demarais et al. |
| 2007/0156135 A1 | 7/2007 | Rubinsky et al. |
| 2007/0167740 A1 | 7/2007 | Grunewald et al. |
| 2007/0167940 A1 | 7/2007 | Stevens-Wright |
| 2007/0173878 A1 | 7/2007 | Heuser |
| 2007/0208329 A1 | 9/2007 | Ward et al. |
| 2007/0225589 A1 | 9/2007 | Viswanathan |
| 2007/0249923 A1 | 10/2007 | Keenan |
| 2007/0260223 A1 | 11/2007 | Scheibe et al. |
| 2007/0270792 A1 | 11/2007 | Hennemann et al. |
| 2008/0009855 A1 | 1/2008 | Hamou |
| 2008/0033426 A1 | 2/2008 | Machell |
| 2008/0065061 A1 | 3/2008 | Viswanathan |
| 2008/0086120 A1 | 4/2008 | Mirza et al. |
| 2008/0091195 A1 | 4/2008 | Silwa et al. |
| 2008/0103545 A1 | 5/2008 | Bolea et al. |
| 2008/0132885 A1 | 6/2008 | Rubinsky et al. |
| 2008/0161789 A1 | 7/2008 | Thao et al. |
| 2008/0172048 A1 | 7/2008 | Martin et al. |
| 2008/0200913 A1 | 8/2008 | Viswanathan |
| 2008/0208118 A1 | 8/2008 | Goldman |
| 2008/0243214 A1 | 10/2008 | Koblish |
| 2008/0281322 A1 | 11/2008 | Sherman et al. |
| 2008/0300574 A1 | 12/2008 | Belson et al. |
| 2008/0300588 A1 | 12/2008 | Groth et al. |
| 2009/0024084 A1 | 1/2009 | Khosla et al. |
| 2009/0048591 A1 | 2/2009 | Ibrahim et al. |
| 2009/0062788 A1 | 3/2009 | Long et al. |
| 2009/0076500 A1 | 3/2009 | Azure |
| 2009/0105654 A1 | 4/2009 | Kurth et al. |
| 2009/0138009 A1 | 5/2009 | Viswanathan et al. |
| 2009/0149917 A1 | 6/2009 | Whitehurst et al. |
| 2009/0163905 A1 | 6/2009 | Winkler et al. |
| 2009/0228003 A1 | 9/2009 | Sinelnikov |
| 2009/0240248 A1 | 9/2009 | Deford et al. |
| 2009/0275827 A1 | 11/2009 | Aiken et al. |
| 2009/0281477 A1 | 11/2009 | Mikus et al. |
| 2009/0306651 A1 | 12/2009 | Schneider |
| 2010/0004623 A1 | 1/2010 | Hamilton et al. |
| 2010/0023004 A1 | 1/2010 | Francischelli et al. |
| 2010/0137861 A1 | 6/2010 | Soroff et al. |
| 2010/0185140 A1 | 7/2010 | Kassab et al. |
| 2010/0185186 A1 | 7/2010 | Longoria |
| 2010/0191112 A1 | 7/2010 | Demarais et al. |
| 2010/0191232 A1 | 7/2010 | Boveda |
| 2010/0241185 A1 | 9/2010 | Mahapatra et al. |
| 2010/0261994 A1 | 10/2010 | Davalos et al. |
| 2010/0274238 A1 | 10/2010 | Klimovitch |
| 2010/0280513 A1 | 11/2010 | Juergen et al. |
| 2010/0280539 A1 | 11/2010 | Miyoshi et al. |
| 2010/0292687 A1 | 11/2010 | Kauphusman et al. |
| 2010/0312096 A1 | 12/2010 | Guttman et al. |
| 2010/0312300 A1 | 12/2010 | Ryu et al. |
| 2011/0028962 A1 | 2/2011 | Werneth et al. |
| 2011/0028964 A1 | 2/2011 | Edwards |
| 2011/0040199 A1 | 2/2011 | Hopenfeld |
| 2011/0098694 A1 | 4/2011 | Long |
| 2011/0106221 A1 | 5/2011 | Neal, II et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190659 A1 | 8/2011 | Long et al. |
| 2011/0190727 A1 | 8/2011 | Edmunds et al. |
| 2011/0213231 A1 | 9/2011 | Hall et al. |
| 2011/0276047 A1 | 11/2011 | Sklar et al. |
| 2011/0276075 A1 | 11/2011 | Fung et al. |
| 2011/0288544 A1 | 11/2011 | Verin et al. |
| 2011/0288547 A1 | 11/2011 | Morgan et al. |
| 2011/0313417 A1 | 12/2011 | De La Rama et al. |
| 2012/0029512 A1 | 2/2012 | Willard et al. |
| 2012/0046570 A1 | 2/2012 | Villegas et al. |
| 2012/0053581 A1 | 3/2012 | Wittkampf et al. |
| 2012/0059255 A1 | 3/2012 | Paul et al. |

(56) References Cited

U.S. PATENT DOCUMENTS

| | | |
|---|---|---|
| 2012/0071872 A1 | 3/2012 | Rubinsky et al. |
| 2012/0078343 A1 | 3/2012 | Fish |
| 2012/0089089 A1 | 4/2012 | Swain et al. |
| 2012/0095459 A1 | 4/2012 | Callas et al. |
| 2012/0101413 A1 | 4/2012 | Beetel et al. |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De Luca et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0131662 A1 | 5/2013 | Wittkampf |
| 2013/0158538 A1 | 6/2013 | Govari |
| 2013/0158621 A1 | 6/2013 | Ding et al. |
| 2013/0172864 A1 | 7/2013 | Ibrahim et al. |
| 2013/0172875 A1 | 7/2013 | Govari et al. |
| 2013/0184702 A1 | 7/2013 | Neal, II et al. |
| 2013/0218157 A1 | 8/2013 | Callas et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Shih |
| 2014/0051993 A1 | 2/2014 | McGee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0058377 A1 | 2/2014 | Deem et al. |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | De La Rama et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0187916 A1 | 7/2014 | Clark et al. |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0235986 A1 | 8/2014 | Harlev et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0119674 A1 | 4/2015 | Fischell et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0142041 A1 | 5/2015 | Kendale et al. |
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |
| 2015/0321021 A1 | 11/2015 | Tandri et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0000500 A1 | 1/2016 | Salahieh et al. |
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058493 A1 | 3/2016 | Neal, II et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |
| 2016/0095653 A1 | 4/2016 | Lambert et al. |
| 2016/0100797 A1 | 4/2016 | Mahapatra et al. |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1 | 4/2016 | Maor |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |
| 2016/0184003 A1 | 6/2016 | Srimathveeravalli et al. |
| 2016/0184004 A1 | 6/2016 | Hull et al. |
| 2016/0213282 A1 | 7/2016 | Leo et al. |
| 2016/0220307 A1 | 8/2016 | Miller et al. |
| 2016/0235470 A1 | 8/2016 | Callas et al. |
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelsen et al. |
| 2016/0331441 A1 | 11/2016 | Konings |
| 2016/0331459 A1 | 11/2016 | Townley et al. |
| 2016/0354142 A1 | 12/2016 | Pearson et al. |
| 2016/0361109 A1 | 12/2016 | Weaver et al. |
| 2017/0001016 A1 | 1/2017 | De Ridder |
| 2017/0035499 A1 | 2/2017 | Stewart et al. |
| 2017/0042449 A1 | 2/2017 | Deno et al. |
| 2017/0042615 A1 | 2/2017 | Salahieh et al. |

(56) References Cited

U.S. PATENT DOCUMENTS

| | | | |
|---|---|---|---|
| 2017/0056648 A1 | 3/2017 | Syed et al. |
| 2017/0065339 A1 | 3/2017 | Mickelsen |
| 2017/0065340 A1 | 3/2017 | Long |
| 2017/0065343 A1 | 3/2017 | Mickelsen |
| 2017/0071543 A1 | 3/2017 | Basu et al. |
| 2017/0095291 A1 | 4/2017 | Harrington et al. |
| 2017/0105793 A1 | 4/2017 | Cao et al. |
| 2017/0146584 A1 | 5/2017 | Daw et al. |
| 2017/0151029 A1 | 6/2017 | Mickelsen |
| 2017/0172654 A1 | 6/2017 | Wittkampf et al. |
| 2017/0181795 A1 | 6/2017 | Debruyne |
| 2017/0189097 A1 | 7/2017 | Viswanathan et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0001056 A1 | 1/2018 | Leeflang et al. |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0085160 A1 | 3/2018 | Viswanathan et al. |
| 2018/0093088 A1 | 4/2018 | Mickelsen |
| 2018/0168511 A1 | 6/2018 | Hall et al. |
| 2018/0200497 A1 | 7/2018 | Mickelsen |
| 2018/0303488 A1 | 10/2018 | Hill |
| 2018/0311497 A1 | 11/2018 | Viswanathan et al. |
| 2018/0360534 A1 | 12/2018 | Teplitsky et al. |
| 2019/0069950 A1 | 3/2019 | Viswanathan et al. |
| 2019/0151015 A1 | 5/2019 | Viswanathan et al. |
| 2019/0231421 A1 | 8/2019 | Viswanathan et al. |
| 2019/0269912 A1 | 9/2019 | Viswanathan et al. |
| 2019/0336198 A1 | 11/2019 | Viswanathan et al. |
| 2019/0336207 A1 | 11/2019 | Viswanathan |

FOREIGN PATENT DOCUMENTS

| | | |
|---|---|---|
| EP | 0797956 | 6/2003 |
| EP | 1127552 | 6/2006 |
| EP | 1340469 | 3/2007 |
| EP | 1009303 | 6/2009 |
| EP | 2213729 | 8/2010 |
| EP | 2425871 | 3/2012 |
| EP | 1803411 | 8/2012 |
| EP | 2532320 A2 | 12/2012 |
| EP | 2587275 | 5/2013 |
| EP | 2663227 | 11/2013 |
| EP | 1909678 | 1/2014 |
| EP | 2217165 | 3/2014 |
| EP | 2376193 | 3/2014 |
| EP | 2708181 | 3/2014 |
| EP | 2777579 A1 | 9/2014 |
| EP | 2934307 | 10/2015 |
| EP | 2777585 | 6/2016 |
| EP | 2382935 B1 | 3/2018 |
| EP | 3111871 B1 | 3/2018 |
| EP | 3151773 B1 | 4/2018 |
| JP | H06-507797 | 9/1994 |
| JP | H10-510745 | 10/1998 |
| JP | 2000-508196 | 7/2000 |
| JP | 2005-516666 | 6/2005 |
| JP | 2006-506184 | 2/2006 |
| JP | 2007-325935 | 12/2007 |
| JP | 2008-538997 | 11/2008 |
| JP | 2009-500129 | 1/2009 |
| JP | 2011-509158 | 3/2011 |
| JP | 2012-050538 | 3/2012 |
| WO | WO 92/07622 | 5/1992 |
| WO | WO 92/21278 | 12/1992 |
| WO | WO 92/21285 | 12/1992 |
| WO | WO 94/07413 | 4/1994 |
| WO | WO 97/24073 | 7/1997 |
| WO | WO 97/25917 | 7/1997 |
| WO | WO 97/37719 | 10/1997 |
| WO | WO 1999/004851 | 2/1999 |
| WO | WO 1999/022659 | 5/1999 |
| WO | WO 1999/056650 | 11/1999 |
| WO | WO 1999/059486 | 11/1999 |
| WO | WO 2002/056782 | 7/2002 |
| WO | WO 2003/053289 | 7/2003 |
| WO | WO 2003/065916 | 8/2003 |
| WO | WO 2004/045442 | 6/2004 |
| WO | WO 2004/086994 | 10/2004 |
| WO | WO 2005/046487 | 5/2005 |
| WO | WO 2006/115902 | 11/2006 |
| WO | WO 2007/006055 | 1/2007 |
| WO | WO 2007/079438 | 7/2007 |
| WO | WO 2009/082710 | 7/2009 |
| WO | WO 2009/089343 | 7/2009 |
| WO | WO 2009/137800 | 11/2009 |
| WO | WO 2010/014480 | 2/2010 |
| WO | WO 2011/028310 | 3/2011 |
| WO | WO 2011/154805 | 12/2011 |
| WO | WO 2012/051433 | 4/2012 |
| WO | WO 2012/153928 | 11/2012 |
| WO | WO 2013/019385 | 2/2013 |
| WO | WO 2014/025394 | 2/2014 |
| WO | WO 2014/031800 | 2/2014 |
| WO | WO 2014/160832 | 10/2014 |
| WO | WO 2015/066322 | 5/2015 |
| WO | WO 2015/099786 | 7/2015 |
| WO | WO 2015/103530 | 7/2015 |
| WO | WO 2015/103574 | 7/2015 |
| WO | WO 2015/130824 | 9/2015 |
| WO | WO 2015/143327 | 9/2015 |
| WO | WO 2015/171921 | 11/2015 |
| WO | WO 2015/175944 | 11/2015 |
| WO | WO 2015/192018 | 12/2015 |
| WO | WO 2015/192027 | 12/2015 |
| WO | WO 2016/059027 | 4/2016 |
| WO | WO 2016/060983 | 4/2016 |
| WO | WO 2016/081650 | 5/2016 |
| WO | WO 2016/090175 | 6/2016 |
| WO | WO 2017/119934 | 7/2017 |
| WO | WO 2017/120169 | 7/2017 |
| WO | WO 2017/192477 | 11/2017 |
| WO | WO 2017/192495 | 11/2017 |
| WO | WO 2017/218734 | 12/2017 |
| WO | WO 2018/200800 | 11/2018 |

OTHER PUBLICATIONS

Supplementary European Search Report for European Application No. 13827672.0, dated Jul. 11, 2016, 12 pages.

Notice of Reasons for Rejection for Japanese Application No. 2015-526522, dated Mar. 6, 2017, 3 pages.

Office Action for U.S. Appl. No. 14/400,455, dated Mar. 30, 2017, 10 pages.

International Search Report and Written Opinion for International Application No. PCT/US2013/031252, dated Jul. 19, 2013, 12 pages.

International Search Report and Written Opinion for International Application No. PCT/US2015/010138, dated Mar. 26, 2015, 14 pages.

International Preliminary Report on Patentability for International Application No. PCT/US2015/010138, dated Jul. 12, 2016, 9 pages.

Office Action for U.S. Appl. No. 15/201,997, dated Apr. 3, 2017, 6 pages.

International Search Report and Written Opinion for International Application No. PCT/US2015/010223, dated Apr. 10, 2015, 19 pages.

International Preliminary Report on Patentability for International Application No. PCT/US2015/010223, dated Jul. 12, 2016, 12 pages.

International Search Report and Written Opinion for International Application No. PCT/US2015/029734, dated Nov. 24, 2015, 15 pages.

International Search Report and Written Opinion for International Application No. PCT/US2015/031086, dated Oct. 21, 2015, 16 pages.

(56) References Cited

OTHER PUBLICATIONS

International Search Report and Written Opinion for International Application No. PCT/US2015/055105, dated Mar. 1, 2016, 15 pages.
International Search Report and Written Opinion for International Application No. PCT/US2015/035582, dated Oct. 2, 2015, 17 pages.
International Search Report and Written Opinion for International Application No. PCT/US2015/035592, dated Oct. 2, 2015, 13 pages.
International Search Report and Written Opinion for International Application No. PCT/US2016/057664, dated Feb. 24, 2017, 11 pages.
Du Pre, B.C. et al., "Minimal coronary artery damage by myocardial electroporation ablation," Europace, 15(1):144-149 (2013).
Hobbs, E. P., "Investor Relations Update: Tissue Ablation via Irreversible Electroporation (IRE)," Powerpoint (2004), 16 pages.
Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].
Madhavan, M. et al., "Novel Percutaneous Epicardial Autonomic Modulation in the Canine for Atrial Fibrillation: Results of an Efficacy and Safety Study," Pace, 00:1-11 (2016).
Neven, K. et al., "Safety and Feasibility of Closed Chest Epicardial Catheter Ablation Using Electroporation," Circ Arrhythm Electrophysiol., 7:913-919 (2014).
Neven, K. et al., "Myocardial Lesion Size After Epicardial Electroporation Catheter Ablation After Subxiphoid Puncture," Circ Arrhythm Electrophysiol., 7(4):728-733 (2014).
Neven, K. et al., "Epicardial linear electroporation ablation and lesion size," Heart Rhythm, 11:1465-1470 (2014).
Van Driel, V.J.H.M. et al., "Pulmonary Vein Stenosis After Catheter Ablation Electroporation Versus Radiofrequency," Circ Arrhythm Electrophysiol., 7(4):734-738 (2014).
Van Driel, V.J.H.M. et al., "Low vulnerability of the right phrenic nerve to electroporation ablation," Heart Rhythm, 12:1838-1844 (2015).
Wittkampf, F.H. et al., "Myocardial Lesion Depth With Circular Electroporation Ablation," Circ. Arrhythm Electrophysiol., 5(3):581-586 (2012).
Wittkampf, F.H. et al., "Feasibility of Electroporation for the Creation of Pulmonary Vein Ostial Lesions," J Cardiovasc Electrophysiol, 22(3):302-309 (Mar. 2011).
Office Action for European Application No. 13827672.0, dated Feb. 5, 2018, 6 pages.
Office Action for U.S. Appl. No. 15/819,726, dated Jun. 4, 2018, 17 pages.
Office Action for U.S. Appl. No. 15/917,194, dated Jun. 4, 2018, 17 pages.
Office Action for U.S. Appl. No. 15/917,194, dated Oct. 9, 2018, 13 pages.
First Office Action for Chinese Application No. 201580006848.8, dated Jan. 29, 2018, 8 pages.
Office Action for European Application No. 15701856.5, dated Dec. 11, 2017, 6 pages.
Notice of Reasons for Rejection for Japanese Application No. 2016-544072, dated Oct. 1, 2018, 6 pages.
Office Action for U.S. Appl. No. 15/201,997, dated Jul. 12, 2018, 12 pages.
Office Action for U.S. Appl. No. 15/795,062, dated Dec. 19, 2017, 14 pages.
Office Action for U.S. Appl. No. 15/795,062, dated Apr. 9, 2018, 20 pages.
Office Action for U.S. Appl. No. 15/795,075, dated Feb. 6, 2018, 9 pages.
Office Action for U.S. Appl. No. 15/795,075, dated Jun. 15, 2018, 10 pages.
Extended European Search Report for European Application No. 15849844.4, dated May 3, 2018, 8 pages.
Office Action for U.S. Appl. No. 15/796,255, dated Jan. 10, 2018, 12 pages.
Extended European Search Report for European Application No. 15806855.1, dated Jan. 3, 2018, 8 pages.
Extended European Search Report for European Application No. 15806278.6, dated Feb. 9, 2018, 5 pages.
Office Action for U.S. Appl. No. 15/796,375, dated Jan. 24, 2018, 25 pages.
Office Action for U.S. Appl. No. 15/796,375, dated May 30, 2018, 26 pages.
Office Action for U.S. Appl. No. 15/796,375, dated Nov. 16, 2018, 27 pages.
Office Action for U.S. Appl. No. 15/711,266, dated Feb. 23, 2018, 14 pages.
International Search Report and Written Opinion for International Application No. PCT/US2017/037609, dated Nov. 8, 2017, 13 pages.
Office Action for U.S. Appl. No. 15/672,916, dated Feb. 13, 2018, 16 pages.
Office Action for U.S. Appl. No. 15/672,916, dated Jul. 20, 2018, 23 pages.
Office Action for U.S. Appl. No. 15/499,804, dated Jan. 3, 2018, 20 pages.
Office Action for U.S. Appl. No. 15/794,717, dated Feb. 1, 2018, 10 pages.
International Search Report and Written Opinion for International Application No. PCT/US2018/029552, dated Jun. 29, 2018, 13 pages.
Office Action for U.S. Appl. No. 15/970,404, dated Oct. 9, 2018, 21 pages.
Office Action for Japanese Application No. 2018-036714, dated Jan. 16, 2019, 8 pages.
Office Action for U.S. Appl. No. 15/201,997, dated Dec. 17, 2018, 17 pages.
Office Action for U.S. Appl. No. 15/341,523, dated Jan. 29, 2019, 10 pages.
Partial European Search Report for European Application No. 18170210.1, dated Feb. 14, 2019, 13 pages.
International Search Report and Written Opinion for International Application No. PCT/US2018/050660, dated Nov. 26, 2018, 13 pages.
Supplementary European Search Report for European Application No. 15733297.4, dated Aug. 10, 2017, 7 pages.
Office Action for U.S. Appl. No. 15/201,997, dated Aug. 29, 2017, 12 pages.
Office Action for U.S. Appl. No. 15/334,646, dated Jul. 25, 2017, 19 pages.
Office Action for U.S. Appl. No. 15/334,646, dated Nov. 16, 2017, 26 pages.
International Search Report and Written Opinion for International Application No. PCT/US2017/012099, dated May 18, 2017, 17 pages.
Office Action for Canadian Application No. 2,881,462, dated Mar. 19, 2019, 5 pages.
Office Action for U.S. Appl. No. 15/917,194, dated Apr. 29, 2019, 10 pages.
Office Action for U.S. Appl. No. 15/201,983, dated Apr. 3, 2019, 16 pages.
Office Action for U.S. Appl. No. 15/341,512, dated Aug. 1, 2019, 19 pages.
Extended European Search Report for European Application No. 18189811.5, dated May 14, 2019, 7 pages.
Office Action for U.S. Appl. No. 15/795,062, dated May 3, 2019, 21 pages.
Office Action for U.S. Appl. No. 15/341,523, dated Jul. 30, 2019, 8 pages.
Office Action for U.S. Appl. No. 15/795,075, dated Apr. 10, 2019, 11 pages.
Office Action for U.S. Appl. No. 15/795,075, dated Jul. 31, 2019, 12 pages.
Office Action for U.S. Appl. No. 15/484,969, dated Sep. 4, 2019, 12 pages.

(56) References Cited

OTHER PUBLICATIONS

Extended European Search Report for European Application No. 16884132.8, dated Jul. 8, 2019, 7 pages.
Office Action for U.S. Appl. No. 16/416,677, dated Aug. 15, 2019, 8 pages.
Extended European Search Report for European Application No. 17736218.3 dated Aug. 23, 2019, 9 pages.
International Search Report and Written Opinion for International Application No. PCT/US2018/029938, dated Aug. 29, 2018, 14 pages.
Office Action for U.S. Appl. No. 16/181,027, dated Sep. 4, 2019, 12 pages.
International Search Report and Written Opinion for International Application No. PCT/US2019/014226, dated Apr. 29, 2019, 15 pages.
Office Action for U.S. Appl. No. 16/240,066, dated May 29, 2019, 7 pages.
Office Action for U.S. Appl. No. 16/375,561, dated Oct. 17, 2019, 15 pages.
Office Action for U.S. Appl. No. 15/672,916, dated Apr. 9, 2019, 31 pages.
Extended European Search Report for European Application No. 18170210.1, dated May 17, 2019, 11 pages.
Office Action for U.S. Appl. No. 15/970,404, dated Apr. 12, 2019, 20 pages.
International Search Report and Written Opinion for International Application No. PCT/US2019/028943, dated Sep. 17, 2019, 17 pages.
International Search Report and Written Opinion for International Application No. PCT/US2019/017322, dated May 10, 2019, 15 pages.
International Search Report and Written Opinion for International Application No. PCT/US2019/030922, dated Sep. 6, 2019, 12 pages.
International Search Report and Written Opinion for International Application No. PCT/US2019/030882, dated Sep. 10, 2019, 17 pages.
Office Action for U.S. Appl. No. 16/405,515, dated Sep. 6, 2019, 9 pages.
International Search Report and Written Opinion for International Application No. PCT/US2019/031135, dated Aug. 5, 2019, 11 pages.
Office Action for U.S. Appl. No. 15/341,512, dated Nov. 12, 2019, 18 pages.
Office Action for U.S. Appl. No. 15/970,404, dated Nov. 12, 2019, 19 pages.
Extended European Search Report for European Application No. 19182099.2, dated Dec. 13, 2019, 7 pages.
Office Action for Japanese Application No. 2018-036714, dated Nov. 27, 2019, 5 pages.
Office Action for U.S. Appl. No. 15/917,194, dated Dec. 20, 2019, 10 pages.
Office Action for U.S. Appl. No. 15/201,983, dated Nov. 15, 2019, 15 pages.
Office Action for U.S. Appl. No. 15/795,062, dated Nov. 4, 2019, 23 pages.
Office Action for U.S. Appl. No. 16/573,704, dated Dec. 17, 2019, 6 pages.

\* cited by examiner

METHOD AND APPARATUS FOR RAPID AND SELECTIVE TISSUE ABLATION WITH COOLING

CROSS-REFERENCE TO RELATED APPLICATIONS

This application is a continuation of PCT Application No. PCT/US2015/035582 titled "METHOD AND APPARATUS FOR RAPID AND SELECTIVE TISSUE ABLATION WITH COOLING, filed Jun. 12, 2015, which claims the benefit of priority to U.S. Provisional Application Ser. No. 61/997,869, entitled "Methods and Apparatus for Rapid and Selective Tissue Ablation with Cooling," filed Jun. 12, 2014, the entire disclosures of which are incorporated herein by reference in their entirety.

BACKGROUND

The embodiments described herein relate generally to medical devices for therapeutic electrical energy delivery, and more particularly to systems and methods for delivering electrical energy in the context of ablating tissue rapidly and selectively by the application of suitably timed pulsed voltages that generate irreversible electroporation of cell membranes, in conjunction with the application of suitable regional cooling to enhance electroporation selectivity and efficacy.

In the past decade or two the technique of electroporation has advanced from the laboratory to clinical applications, while the effects of brief pulses of high voltages and large electric fields on tissue has been investigated for the past forty years or more. It has been known that the application of brief high DC voltages to tissue, thereby generating locally high electric fields typically in the range of hundreds of Volts/centimeter can disrupt cell membranes by generating pores in the cell membrane. While the precise mechanism of this electrically-driven pore generation or electroporation is not well understood, it is thought that the application of relatively large electric fields generates instabilities in the lipid bilayers in cell membranes, causing the occurrence of a distribution of local gaps or pores in the membrane. If the applied electric field at the membrane is larger than a threshold value, the electroporation is irreversible and the pores remain open, permitting exchange of material across the membrane and leading to apoptosis or cell death. Subsequently the tissue heals in a natural process.

Some known processes of adipose tissue reduction by freezing, also known as cryogenically induced lipolysis, can involve a significant length of therapy time. In contrast, the action of irreversible electroporation can be much more rapid. Some known tissue ablation methods employing irreversible electroporation, however, involve destroying a significant mass of tissue, and one concern the temperature increase in the tissue resulting from this ablation process.

While pulsed DC voltages are known to drive irreversible electroporation under the right circumstances, the examples of electroporation applications in medicine and delivery methods described in the prior art do not sufficiently discuss specificity and rapidity of action, or methods to treat a local region of tissue with irreversible electroporation while not applying electroporation to adjoining regions of tissue.

Thus, there is a need for selective energy delivery for electroporation and its modulation in various tissue types as well as pulses that permit rapid action and completion of therapy delivery. There is also a need for more effective generation of voltage pulses and control methods, as well as appropriate devices or tools addressing a variety of specific clinical applications. Such more selective and effective electroporation delivery methods can broaden the areas of clinical application of irreversible electroporation including therapeutic treatment to reduce the volume of adipose or fat tissue and the treatment of tumors of various types.

SUMMARY

The embodiments described herein address the need for tools and methods for rapid and selective application of irreversible electroporation therapy as well as pulse generation and control methods. The process of irreversible electroporation can be induced even without the flow of current when a polarizing high voltage is applied to generate a suitably large electric field in a region of interest. The embodiments described herein can result in well-controlled and specific delivery of electroporation in an efficacious manner.

In some embodiments, an apparatus includes a clamp, a first electrode head and a second electrode head. The clamp includes a first arm and a second arm, each configured to exert opposing forces to maintain a target tissue disposed therebetween. The first electrode head is coupled to the first arm. The first electrode head includes a first electrically insulating contact surface, a first electrode and a first cooling unit. The first contact surface is configured to contact a first portion of the target tissue. The first cooling unit is configured to maintain the first portion of the target tissue at a first target temperature. The second electrode head is coupled to the second arm, and includes a second electrically insulating contact surface, a second electrode and a second cooling unit. The second contact surface is configured to contact a second portion of the target tissue. The second cooling unit is configured to maintain the second portion of the target tissue at a second target temperature. The first electrode and the second electrode are collectively configured to deliver a voltage pulse to the target tissue.

DETAILED DESCRIPTION

Figure 1A:
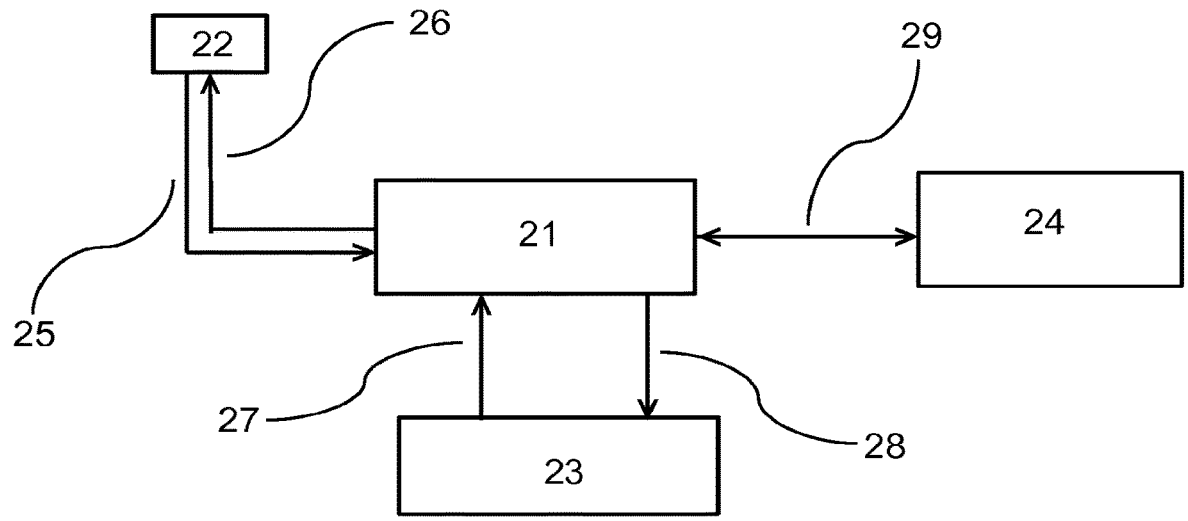
FIG. 1A is a schematic illustration of an irreversible electroporation system that includes a DC voltage/signal generator, a controller capable of being configured to apply voltages to selected subsets of electrodes, and one or more medical devices connected to the controller.

Medical systems, tools and methods are disclosed for the selective and rapid application of DC voltage to drive electroporation. In some embodiments, an apparatus includes a clamp, a first electrode head and a second electrode head. The clamp includes a first arm and a second arm, each configured to exert opposing forces to maintain a target tissue disposed therebetween. The first electrode head is coupled to the first arm. The first electrode head includes a first electrically insulating contact surface, a first electrode and a first cooling unit. The first contact surface is configured to contact a first portion of the target tissue. The first cooling unit is configured to maintain the first portion of the target tissue at a first target temperature. The second electrode head is coupled to the second arm, and includes a second electrically insulating contact surface, a second electrode and a second cooling unit. The second contact surface is configured to contact a second portion of the target tissue. The second cooling unit is configured to maintain the second portion of the target tissue at a second target temperature. The first electrode and the second electrode are collectively configured to deliver a voltage pulse to the target tissue.

In some embodiments, an apparatus includes a voltage pulse generator configured to produce a pulsed voltage waveform, and an electrode controller. The electrode controller is configured to be operably coupled to the voltage pulse generator and a medical clamp. The medical clamp includes a plurality of electrodes. The electrode controller is implemented in at least one of a memory or a processor, and includes a feedback module, a cooling module and a pulse delivery module. The feedback module is configured to determine a temperature of a target tissue to which the medical clamp is coupled. The cooling module is configured to produce a signal to a cooling unit of the medical clamp to maintain a portion of the target tissue at a target temperature. The pulse delivery module is configured to deliver an output signal associated with the pulsed voltage waveform to the plurality of electrodes.

In some embodiments, a non-transitory processor readable medium storing code representing instructions to be executed by a processor includes code to cause the processor to determine a temperature of a target tissue to which a medical clamp is coupled. The medical clamp includes a plurality of electrodes. The code further includes code to produce a signal based at least in part on the temperature of the target tissue. The signal is delivered to a cooling unit of the medical clamp to maintain a portion of the target tissue at a target temperature. The code further includes code to deliver an output signal associated with the pulsed voltage waveform to the plurality of electrodes when the target tissue is at the target temperature.

In some embodiments, a method includes receiving, at a feedback module of an electrode controller, a signal associated with a temperature of a target tissue to which a medical clamp is coupled. The medical clamp includes a plurality of electrodes. A signal based at least in part on the temperature of the target tissue is produced. The signal is then delivered to a cooling unit of the medical clamp to maintain a portion of the target tissue at a target temperature. The method includes delivering an output signal associated with the pulsed voltage waveform to the plurality of electrodes when the target tissue is at the target temperature.

In some embodiments, an irreversible electroporation system includes a DC voltage/signal generator and a controller capable of being configured to apply voltages to a selected multiplicity of electrodes. Further, the controller is capable of applying control inputs whereby selected pairs of anode-cathode subsets of electrodes can be sequentially updated based on a pre-determined sequence. In some embodiments, the controller can further receive at least one temperature input, and based on a temperature input the controller can modify or update a control parameter that can help to maintain a temperature value near a region of interest. The generator can output waveforms that can be selected to generate a sequence of voltage pulses in either monophasic or biphasic forms and with either constant or progressively changing amplitudes.

Devices are disclosed for the selective electroporation ablation of particular tissue type (e.g., adipose tissue) while preserving surrounding tissue of other types. In some embodiments, the system can include a means for sensing electrode separation, and the electrode voltage applied can be determined based on a sensed separation or distance measure. This determination can be fully or partially automatic, or manual.

In some embodiments, a system uses temperature to selectively ablate tissue as the threshold of irreversible electroporation is temperature-dependent, utilizing means such as the suitable use of cooling fluid or solid state cooling methods to locally raise the irreversible electroporation threshold electric field value and thereby selecting the predominant tissue type or region it is desired to ablate. In contrast to the process of adipose tissue reduction by freezing, also known as cryogenically induced lipolysis, which uses lower temperatures to directly freeze adipose tissue, the lowered temperatures according to an embodiment assist in the selective action of irreversible electroporation, a much more rapid process than freezing.

In some embodiments, an irreversible electroporation system includes a DC voltage/signal generator and a controller that is configured to apply voltages to a selected multiplicity or a subset of electrodes. In some embodiments, a temperature measurement device such as a thermistor measures temperature at or near a portion of an electrode device. The controller is capable of applying control inputs whereby the temperature at or near a portion of the device is maintained within a narrow range of desired values. Preferably, the temperature at or near an electrode or electrode head surface contacting a patient anatomy is maintained at or near a value that is lower than body temperature. In some embodiments, the application of DC voltage pulses is made only when the temperature is within a narrow range of values around a desired value. In some embodiments, at least one control input for temperature control takes the form of rate of flow of a cooling fluid, while in another embodiment, the control input is a voltage that drives a thermoelectric heat pump. Further, in some embodiments, the electrode clamp device disclosed here incorporates a sensor to measure a separation distance, based on which the electroporation voltage value is selected.

A DC voltage for electroporation can be applied to subsets of electrodes identified as anode and cathode respectively on opposite sides of an anatomical region it is desired to ablate. The DC voltage is applied in brief pulses sufficient to cause irreversible electroporation and can preferably be in the range of 0.5 kV to 60 kV and more preferably in the range 1 kV to 10 kV, so that an appropriate threshold electric field value of at least around 800 Volts/cm is effectively achieved in the tissue (for example, adipose tissue) to be ablated. In some embodiments, the DC voltage generator setting for irreversible electroporation is automatically identified by the electroporation system based on a sensed distance measuring the spatial separation between electrodes of opposing polarities. In an alternate embodiment, the DC voltage value is selected directly by a user from a suitable dial, slider, touch screen, or any other user interface. In some embodiments, while transient currents may be induced in the tissue upon voltage application or removal, there are no other (steady state) currents as the electrodes are insulated from the subject anatomy. A region or volume of tissue where the electric field is sufficiently large for irreversible electroporation to occur is ablated during the DC voltage pulse application. At the same time, the application of surface cooling raises the electroporation threshold of tissue near the surface and prevents the occurrence of irreversible electroporation in this surface layer.

As used in this specification, the singular forms "a," "an" and "the" include plural referents unless the context clearly dictates otherwise. Thus, for example, the term "a member" is intended to mean a single member or a combination of members, "a material" is intended to mean one or more materials, "a processor" is intended to mean a single processor or multiple processors; and "memory" is intended to mean one or more memories, or a combination thereof.

As used herein, the terms "about" and "approximately" generally mean plus or minus 10% of the value stated. For example, about 0.5 would include 0.45 and 0.55, about 10 would include 9 to 11, about 1000 would include 900 to 1100.

A schematic diagram of the electroporation system according to an embodiment is shown in FIG. 1A. The system includes a DC voltage/signal generator 23 is driven by a controller unit 21 that interfaces with a computer device 24 by means of a two-way communication link 29. The controller can perform channel selection and routing functions for applying DC voltages to appropriate electrodes that have been selected by a user or by the computer 24, and apply the voltages via a multiplicity of leads (shown collectively as 26) to an electrode device 22. The electrode device 22, and any of the electrode devices described herein can be similar to the ablation catheters described in PCT Publication No. WO2014/025394, entitled "Catheters, Catheter Systems, and Methods for Puncturing Through a Tissue Structure," filed on Mar. 14, 2013 ("the '394 PCT Application), which is incorporated herein by reference in its entirety.

Some of the leads 26 from the controller 21 can also carry control signals to adjust temperature at or near the electrode device. In an alternate embodiment, the control signals from the controller 21 can be routed to a different unit (not shown) such as a cooling pump for example, to control cooling fluid flow rate). The electrode device 22 can also send information and/or signals to the controller 21, such as temperature data from sensors mounted on or near the electrode device. Such feedback signals are indicated by the data stream 25, which can be sent via separate leads. While the DC voltage generator 23 sends a DC voltage to the controller 21 through leads 27, the voltage generator is driven by control and timing inputs 28 from the controller unit 21.

Figure 1B:
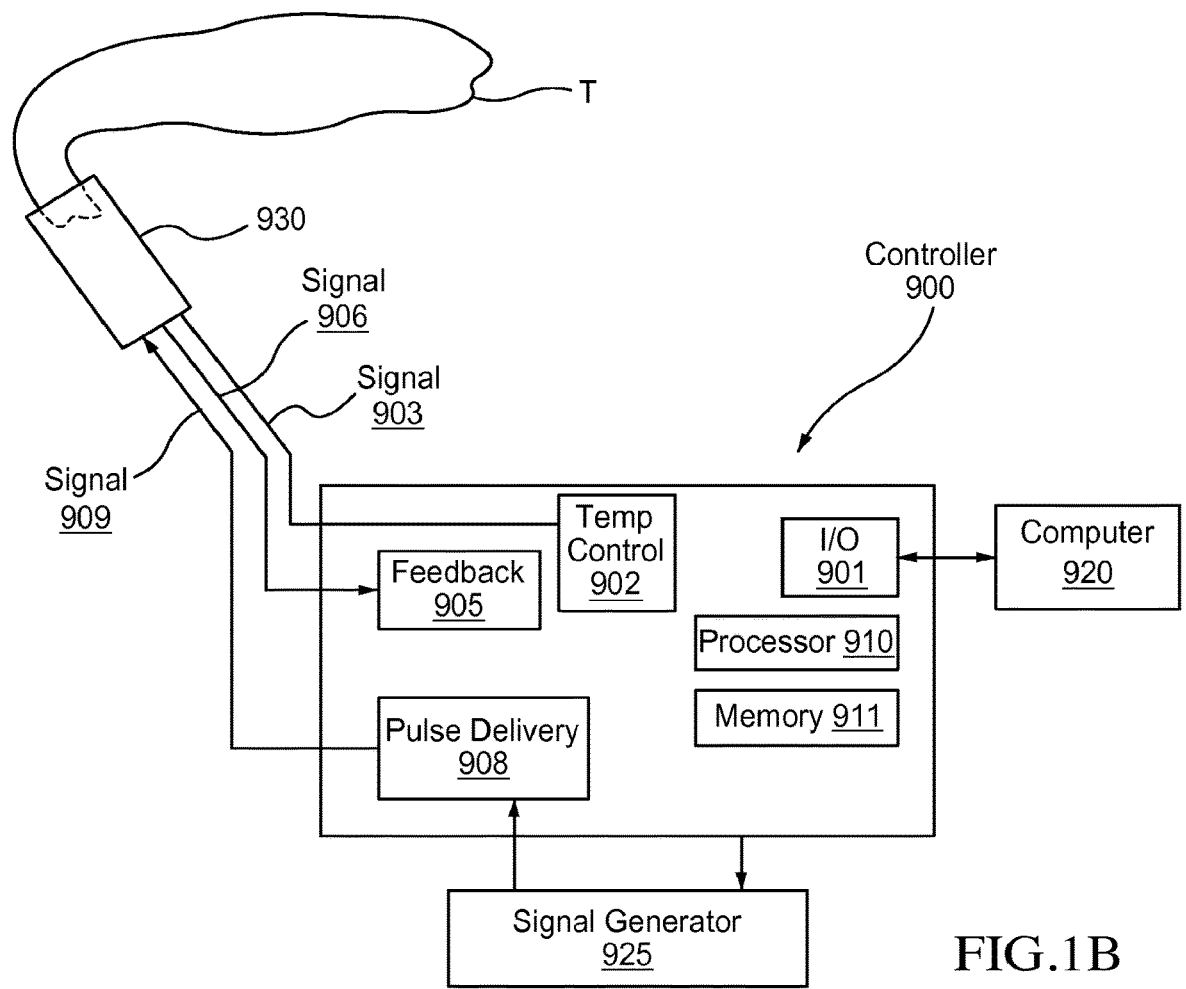
FIG. 1B is a schematic illustration of an irreversible electroporation system that includes a DC voltage/signal generator and a controller according to an embodiment.

In some embodiments, the electrode controller can include one or more modules and can automatically control the temperature of a target tissue, adjust a characteristic of the voltage waveform based on the spacing between adjacent electrodes, or the like. For example, FIG. 1B shows an electroporation system according to an embodiment that includes an electrode controller 900 and a signal generator 925. The electrode controller 900 is coupled to a computer 920 or other input/output device, and is configured to be operably coupled to a medical device 930. The medical device 930 can be one or more of the medical clamps of the types shown and described herein. Further the medical device 930 can be coupled to, disposed about and/or in contact with a target tissue T. In this manner, as described herein, the electroporation system, including the electrode controller 900 and the signal generator 925, can deliver voltage pulses to the target tissue for therapeutic purposes.

The controller 900 can include a memory 911, a processor 910, and an input/output module (or interface) 901. The controller 900 can also include a temperature control module 902, a feedback module 905, and a pulse delivery module 908. The electrode controller 900 is coupled to a computer 920 or other input/output device via the input/output module (or interface) 901.

The processor 910 can be any processor configured to, for example, write data into and read data from the memory 911, and execute the instructions and/or methods stored within the memory 911. Furthermore, the processor 910 can be configured to control operation of the other modules within the controller (e.g., the temperature control module 902, the feedback module 905, and the pulse delivery module 908). Specifically, the processor 910 can receive a signal including user input, temperature data, distance measurements or the like and determine a set of electrodes to which voltage pulses should be applied, the desired timing and sequence of the voltage pulses and the like. In other embodiments, the processor 910 can be, for example, an application-specific integrated circuit (ASIC) or a combination of ASICs, which are designed to perform one or more specific functions. In yet other embodiments, the microprocessor can be an analog or digital circuit, or a combination of multiple circuits.

The memory device 911 can be any suitable device such as, for example, a read only memory (ROM) component, a random access memory (RAM) component, electronically programmable read only memory (EPROM), erasable electronically programmable read only memory (EEPROM), registers, cache memory, and/or flash memory. Any of the modules (the temperature control module 902, the feedback module 905, and the pulse delivery module 908) can be implemented by the processor 910 and/or stored within the memory 911.

As shown, the electrode controller 900 operably coupled to the signal generator 925. The signal generator includes circuitry, components and/or code to produce a series of DC voltage pulses for delivery to electrodes included within the medical device 930. For example, in some embodiments, the signal generator 925 can be configured to produce a biphasic waveform having a pre-polarizing pulse followed by a polarizing pulse. The signal generator 925 can be any suitable signal generator of the types shown and described herein.

The pulse delivery module 908 of the electrode controller 900 includes circuitry, components and/or code to deliver an output signal associated with the pulsed voltage waveform produced by the signal generator 925. This signal (shown as signal 909) can be any signal of the types shown and described herein, and can be of a type and/or have characteristics to be therapeutically effective. In some embodiments, the pulse delivery module 908 receives input from other portions of the system, and can therefore send the signal 909 to the appropriate subset of electrodes, as described herein.

The electrode controller 900 includes the temperature control module 902. The temperature control module 902 includes circuitry, components and/or code to produce a control signal (identified as signal 903) that can be delivered to the cooling unit (not shown) of the medical device 930 to facilitate cooling of a portion of the tissue T.

In some embodiments, the ablation controller and signal generator can be mounted on a rolling trolley, and the user can control the device using a touchscreen interface that could possibly be in the sterile field. The touchscreen can be for example an LCD touchscreen in a plastic housing mountable to a standard medical rail or post and can be used to select the electrodes for ablation and to ready the device to fire. The interface can for example be covered with a clear sterile plastic drape. The operator can select the electrodes involved in an automated sequence, if any. The touch screen graphically shows the catheters that are attached to the controller. In one embodiment the operator can select electrodes from the touchscreen with appropriate graphical buttons. The ablation sequence can be initiated by holding down a hand-held trigger button that is possibly in a sterile field. The hand-held trigger button can be illuminated red to indicate that the device is "armed" and ready to ablate. The trigger button can be compatible for use in a sterile field and when attached to the controller can be illuminated a different color, for example white. In some embodiments, the "armed" state of the trigger can depend on whether the electrode temperature is within a desired range of values; if not, an appropriate control signal is applied to bring the temperature back to the desired range. When the device is firing, the trigger button flashes in sequence with the pulse delivery in a specific color such as red. The waveform of each delivered pulse is displayed on the touchscreen interface.

The waveforms for the various electrodes can be displayed and recorded on the case monitor and simultaneously outputted to a standard data acquisition system. With the high voltages involved with the device, the outputs to the data acquisition system are protected from voltage and/or current surges. The waveform amplitude, period, duty cycle, and delay can all be modified, for example via a suitable Ethernet connection.

In some embodiments, a system (generator and controller) according to an embodiment can deliver rectangular-wave pulses with a peak maximum voltage of up to about 10 kV into a load with an impedance in the range of 30 Ohm to 3000 Ohm for a maximum duration of 200 µs. In some embodiments the maximum duration can be 100 µs. The load can be part of the electrode circuitry, so that power is harmlessly dissipated in the load. Pulses can be delivered in a multiplexed and synchronized manner to a multi-electrode device with a duty cycle of up to 50% (for short bursts). The pulses can generally be delivered in bursts, such as for example a sequence of between 2 and 10 pulses interrupted by pauses of between 1 ms and 1000 ms. In one embodiment, the multiplexer controller is capable of running an automated sequence to deliver the impulses/impulse trains (from the DC voltage signal/impulse generator) to the tissue target as a sequence of pulses over electrodes. The controller system is capable of switching between subsets of electrodes located on the electrode device.

In some embodiments, the controller can have several pulse sequence configurations that provide the operator with at least some variety of programming options. In one configuration, the controller can switch electrode configurations of a bipolar set of electrodes (cathode and anode) sequentially along the length of an electrode clamp device. The user can control the application of DC voltage with a single handheld switch. A sterile catheter or catheters can be connected to the voltage output of the generator via a connector cable. In one embodiment, the user activates the device with a touch screen. The generator can remain in a standby mode until the user is ready to apply pulses at which point the user/assistant can put the generator into a ready mode via the touchscreen interface. Subsequently the user can select the sequence and the active electrodes.

In some embodiments, any of the systems described herein can select an appropriate voltage value based on a distance measurement between electrodes of opposing polarities. In this manner, the system can ensure that an electric field sufficient to cause irreversible electroporation is applied up to the desired depth.

Figure 2:
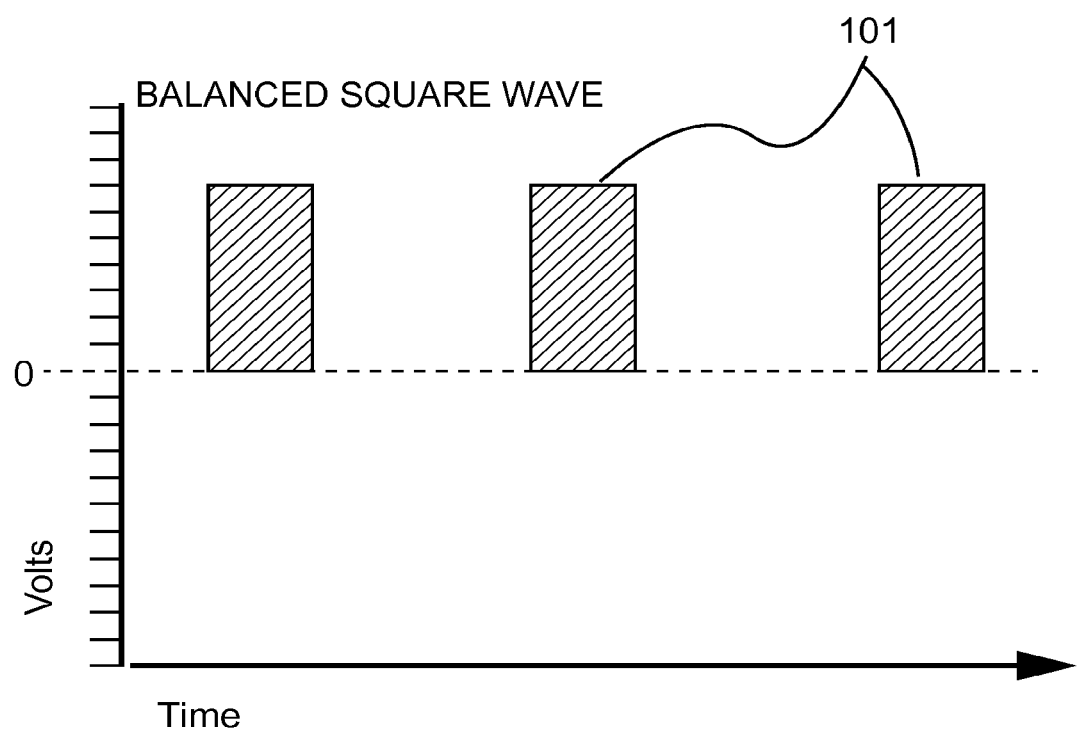
FIG. 2 is a schematic illustration of a waveform generated by the irreversible electroporation system according to an embodiment, showing a balanced rectangular wave.
Figure 3:
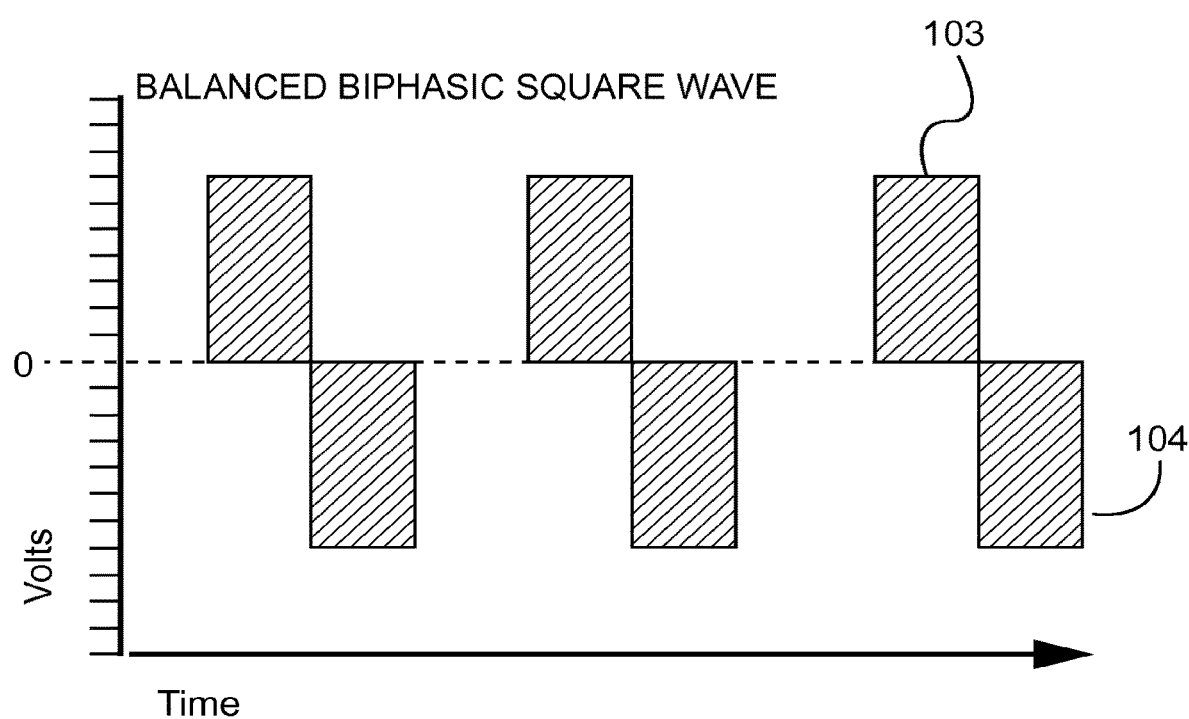
FIG. 3 is a schematic illustration of a waveform generated by the irreversible electroporation system according to an embodiment, showing a balanced biphasic rectangular wave.

The controller and generator can output waveforms that can be selected to generate a sequence of voltage pulses in either monophasic or biphasic forms and with either constant or progressively changing amplitudes. FIG. 2 shows a square or rectangular wave pulse train where the pulses 101 have a uniform height or maximum voltage. FIG. 3 shows an example of a balanced biphasic rectangular pulse train, where each positive voltage pulse such as 103 is immediately followed by a negative voltage pulse such as 104 of equal amplitude and opposite sign. While in this example the biphasic pulses are balanced with equal amplitudes of the positive and negative voltages, in other embodiments an unbalanced biphasic waveform could also be used as may be convenient for a given application.

A train of multiple DC voltage pulses can be applied to ensure that sufficient tissue ablation has occurred. Further, the user can repeat the delivery of irreversible electroporation over several successive pulse trains for further confidence.

Figure 4:
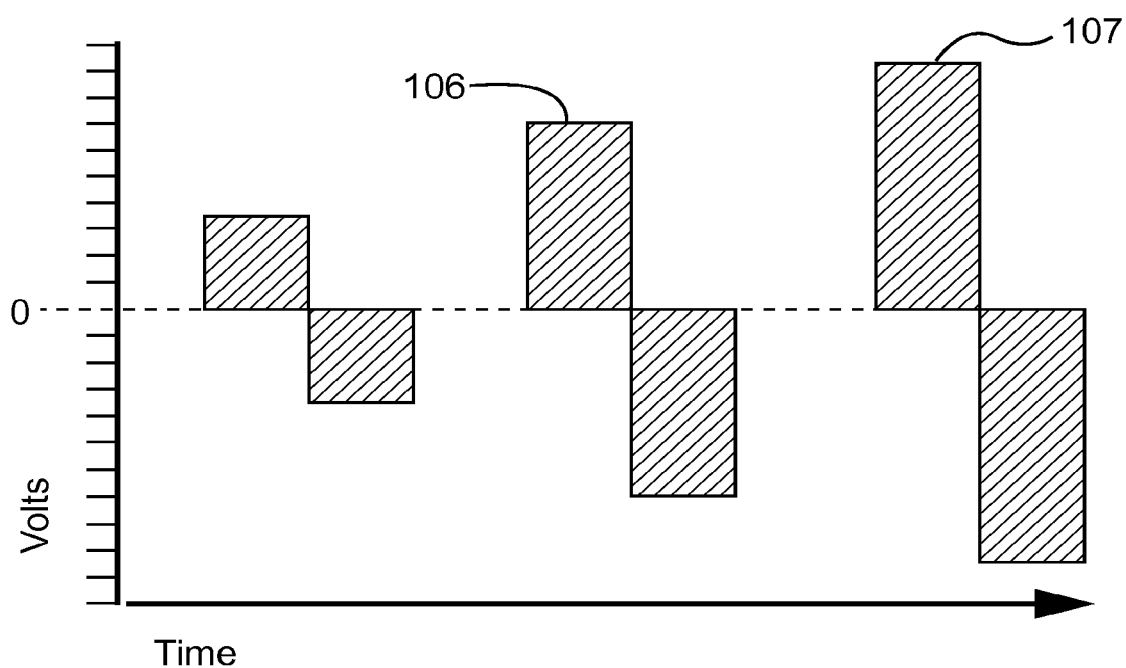
FIG. 4 is a schematic illustration of a waveform generated by the irreversible electroporation system according to an embodiment, showing a progressive balanced biphasic rectangular wave.

Yet another example of a waveform or pulse shape that can be generated by any of the systems described herein is illustrated in FIG. 4, which shows a progressive balanced rectangular pulse train. In this pulse train, each distinct biphasic pulse has equal-amplitude positive and negative voltages, but each pulse such as 107 is larger in amplitude than its immediate predecessor 106. Other variations such as a progressive unbalanced rectangular pulse train, or indeed a wide variety of other variations of pulse amplitude with respect to time can be conceived and implemented by those skilled in the art based on the teachings herein.

The time duration of each irreversible electroporation rectangular voltage pulse could lie in the range from 1 nanosecond to 10 milliseconds, with the range 10 microseconds to 1 millisecond being more preferable and the range 50 microseconds to 300 microseconds being still more preferable. The time interval between successive pulses of a pulse train could be in the range of 10 microseconds to 1 millisecond, with the range 50 microseconds to 300 microseconds being more preferable. The number of pulses applied in a single pulse train (with delays between individual pulses lying in the ranges just mentioned) can range from 1 to 100, with the range 1 to 10 being more preferable. As described in the foregoing, a pulse train can be driven by a user-controlled switch or button, in one embodiment preferably mounted on a hand-held joystick-like device. In one mode of operation a pulse train can be generated for every push of such a control button, while in an alternate mode of operation pulse trains can be generated repeatedly during the refractory periods of a set of successive cardiac cycles, for as long as the user-controlled switch or button is engaged by the user.

All of these parameters can be determined by the design of the signal generator, and in various embodiments could also be determined by user control as may be convenient for a given clinical application. The specific examples and descriptions herein are exemplary in nature and variations can be developed by those skilled in the art based on the material taught herein without departing from the scope according to an embodiment, which is limited only by the attached claims.

Figure 5:
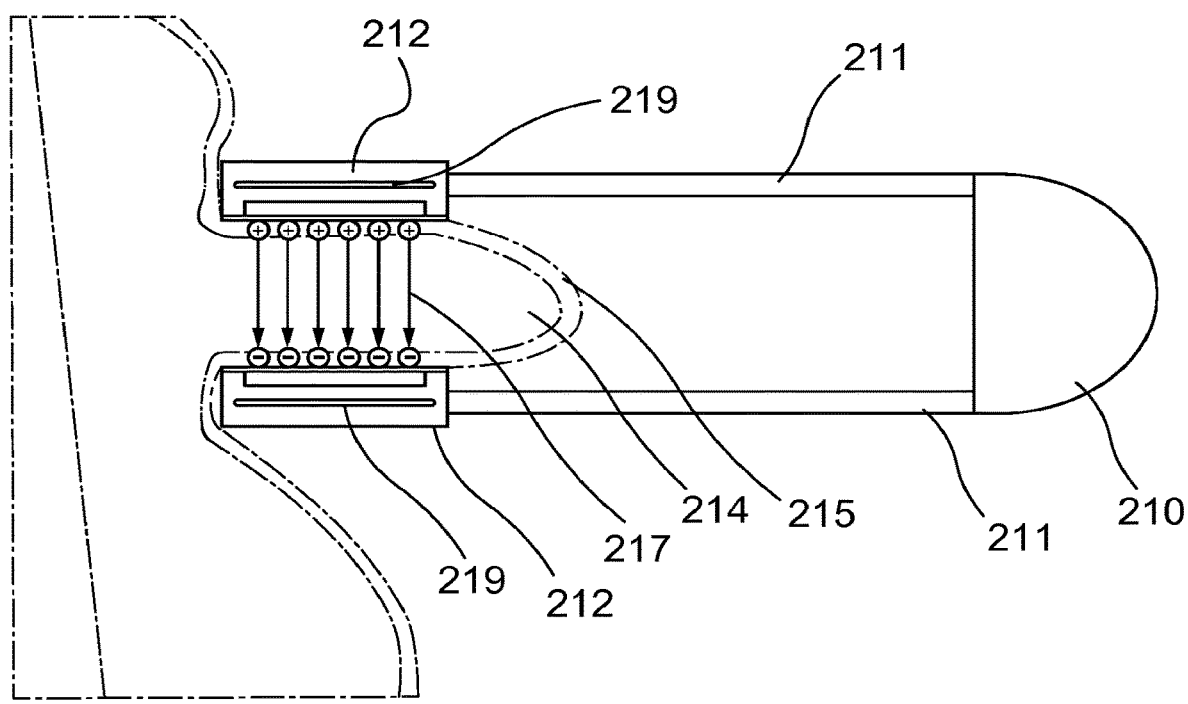
FIG. 5 is a schematic illustration of a fat ablation electrode clamp device according to an embodiment, where an electrode system is schematically shown clamped around target tissue.

In some embodiments, an irreversible electroporation ablation system of the type shown and described herein can be used for adipose tissue (or fat) ablation for the reduction or elimination of adipose tissue. As mentioned earlier, various tissue or cell types have different irreversible electroporation thresholds. Fat cells typically have an irreversible electroporation threshold in the range of 800 Volts/cm. FIG. 5 shows an electrode clamp device that externally clamps onto a fold of skin on a patient anatomy, with electrode clamp arms 211 connected to a clamp head 210 including springs, screw or other tightening mechanisms for firmly positioning the electrodes in a clamped position. The electrode clamp arms end in electrode heads 212 that incorporate cooling coils 219 that carry a cooling fluid at a temperature sufficient to cool and maintain the skin temperature at about approximately 50 degrees Fahrenheit. A cooling system and drive pump (not shown) with a controllable fluid flow rate supply coolant to maintain the electrode temperature at or near a suitably low value (such as, for example, 50 degrees Fahrenheit). The electrodes are shown clamping on to tissue in the form of a layer of skin 215 with fatty tissue 214 beneath the skin. Each electrode itself is located internally within its electrode head and the latter is made of insulating material, so that no conductor touches the patient surface. FIG. 5 shows an example of electric field lines 217 generated in the tissue when a DC voltage is applied across the electrodes.

As shown in FIG. 5, since the patient-contacting surfaces are insulators, there is no steady state charge transfer or direct current within the tissue. However, the polarizing electric field applied in pulses can generate irreversible electroporation in the tissue and generate induced or transient currents in the tissue. The irreversible electroporation threshold of tissue increases as temperature decreases. Thus, by cooling the electrodes and the layer of skin, the skin tissue's electroporation threshold can be increased beyond the approximately 800 V/cm threshold value of fat tissue. When a DC electric field of suitable strength is applied, fat (indicated by 214 in FIG. 5) can therefore be selectively ablated by electroporation while maintaining the integrity of skin tissue (indicated by 215 in FIG. 5) as long as the applied electric field is in the range between the irreversible electroporation thresholds of adipose tissue and the cooled skin tissue.

Figure 6:
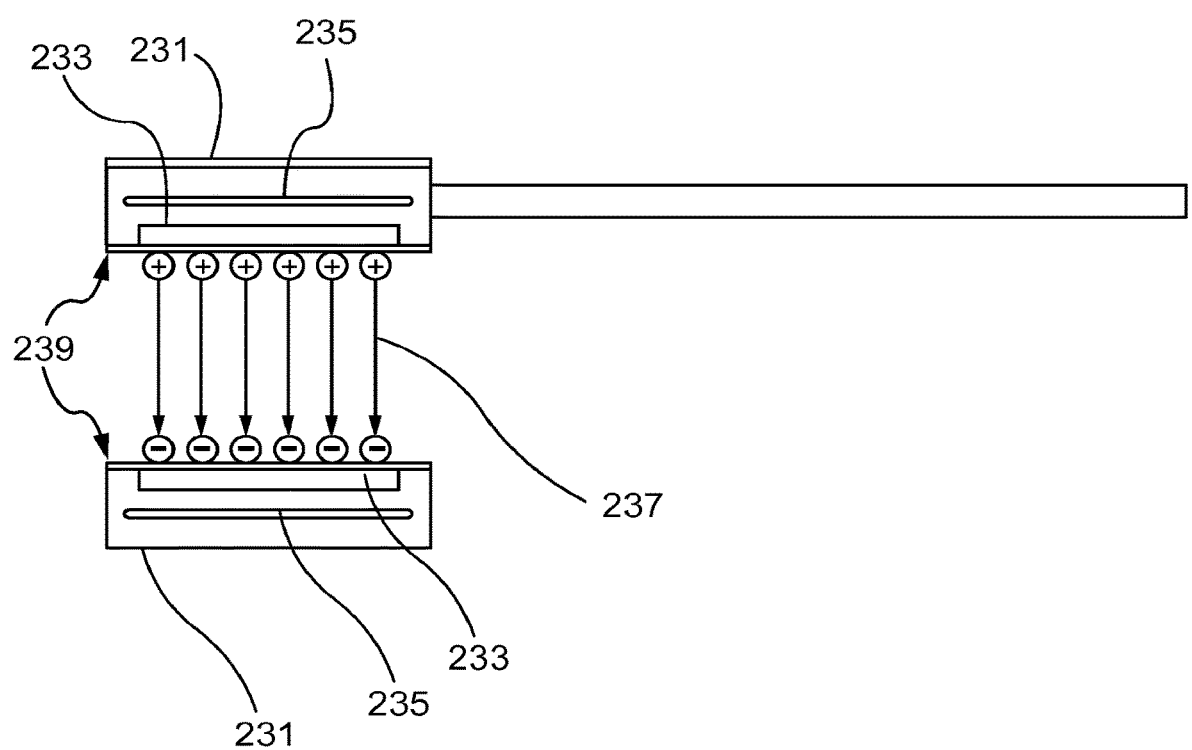
FIG. 6 is a schematic illustration of a fat ablation electrode clamp device according to an embodiment, where different parts of the electrode system are shown schematically.

FIG. 6 is a schematic illustration of an electrode head of the electrode clamp device showing the electrodes or electroporation probes 233 situated within an outer casing 231. Coolant coils 235 within each electrode head keep the electrode head surface cold and maintain the skin temperature at approximately 50 degrees Fahrenheit. The patient-contacting surface 239 of each electrode head is an insulator, so that there is no direct current transfer between the electrodes. The parallel electrodes act like capacitor plates for very brief periods as DC voltage pulses are applied for irreversible electroporation. The electric field 237 generated between the electrodes in the tissue region serves to polarize the tissue and generate irreversible electroporation in the fat or adipose tissue. The voltage pulses induce brief transient currents in the tissue when the field changes but no steady state direct current. Thus with this device, inductive irreversible electroporation can be generated. The applied DC voltage can be made to depend on the distance between the electrodes. In one embodiment, the electrode clamp can have a discrete number of possible relative positions of the electrodes with pre-determined separation distances. Based on the separation, a sufficient voltage that generates at least an approximately 800 Volts/cm electric field between the electrodes can be computed by the electroporation system and applied for the selective irreversible electroporation of adipose tissue.

Figure 7:
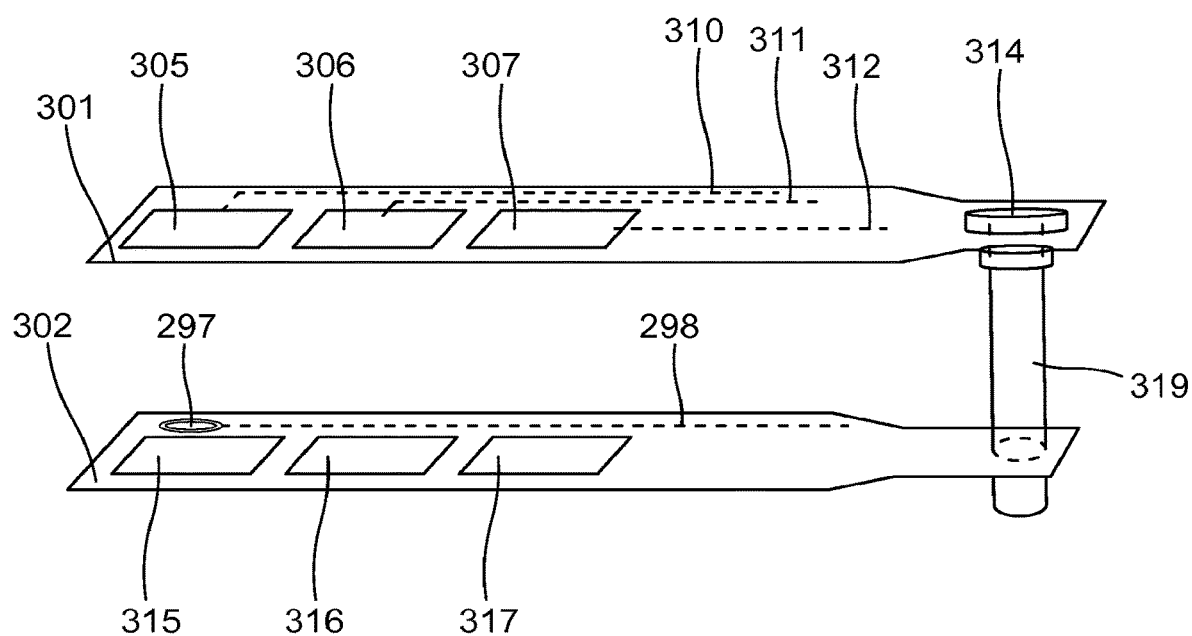
FIG. 7 is a schematic illustration of a fat ablation electrode clamp device according to an embodiment, where multiple electrodes are shown on each clamp, the electrode heads incorporating means for solid state cooling, and including a means for adjusting the separation between electrode clamps.

FIG. 7 shows an electrode clamp device that externally clamps onto a fold of skin on a patient anatomy, with electrode clamp arms 301 and 302 connected to a clamp head 314 including a screw mechanism 319 for firmly positioning the electrodes in a clamped position around a portion of patient anatomy, with a fixed distance between electrode arms. The top electrode arm 301 has disposed along it electrode heads 305, 306 and 307 respectively aligned with electrode heads 315, 316 and 317 on the bottom electrode arm 302. In FIG. 7, the lower electrode arm 302 is fixed to a mount (not shown) and the screw mechanism allows for the vertical motion of electrode arm 301 relative to electrode arm 302, thereby permitting adjustment of the separation distance between the arms over a range of values. In some embodiments, the electrode heads can incorporate thermoelectric cooling modules for keeping the patient-contacting face of each electrode at a cooled temperature significantly below body temperature (for example, the patient contacting face of the electrode can be maintained in a narrow range around 50 degrees Fahrenheit). This can be done with a thermoelectric or solid state cooling module by applying an appropriate voltage or current to the cooling module. Solid state cooling has the advantage of having no moving parts with corresponding convenience of design and implementation.

As an example, referring to FIG. 7 bipolar leads 310, 311 and 312 attach to electrode heads 305, 306 and 307 respectively in order to control the temperature on the patient contacting electrode face of each electrode. When an appropriate voltage is applied across a Peltier cooling module, it functions as a heat pump, transferring heat from one face of the module to the other. Furthermore, each electrode head, or at least each electrode arm, can incorporate a temperature sensing unit such as a thermistor 297 shown attached to leads 298 on electrode arm 302. The data from the temperature sensing unit is read by the controller (not shown in FIG. 7) or to a computer where the temperature data is utilized to generate an appropriate control signal for the purpose of maintaining electrode face temperature by using any of a range of control schemes or methods, for example PID (Proportional-Integral-Derivative) control.

Figure 8:
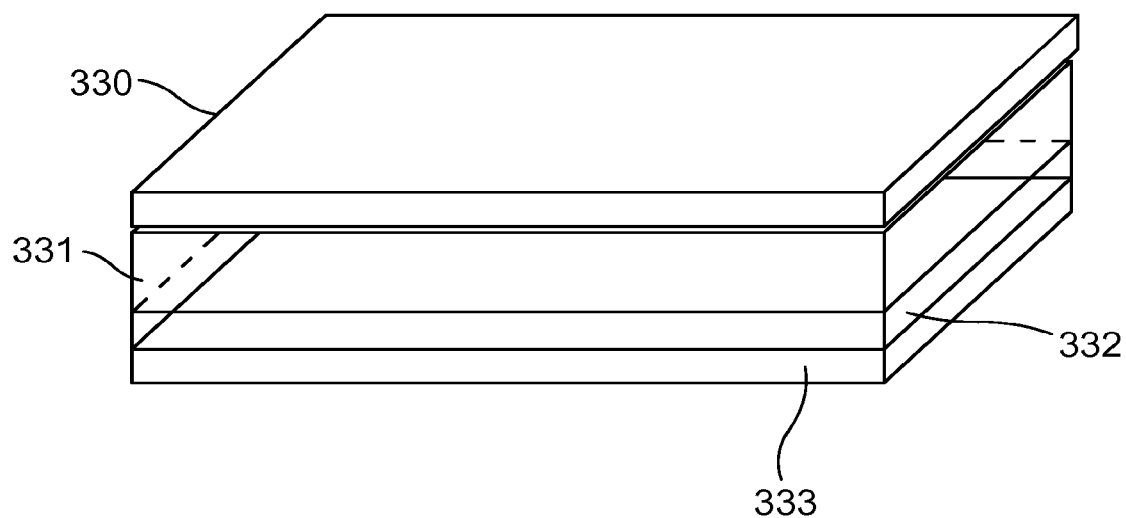
FIG. 8 is a schematic illustration of an electrode head design according to an embodiment incorporating means for solid state cooling.

FIG. 8 is a schematic illustration of an electrode head incorporating means for solid state or thermoelectric cooling. A metal electrode 332 for high voltage DC application abuts a ceramic cover 333 on one side (with the outside face of the ceramic cover being a patient contacting face) and a thermoelectric or Peltier cooling module 331 on the other. The top face of the cooling module 331 is adjacent to a ceramic cover 330, so that the entire electrode head has ceramic faces on both top and bottom faces.

Figure 9:
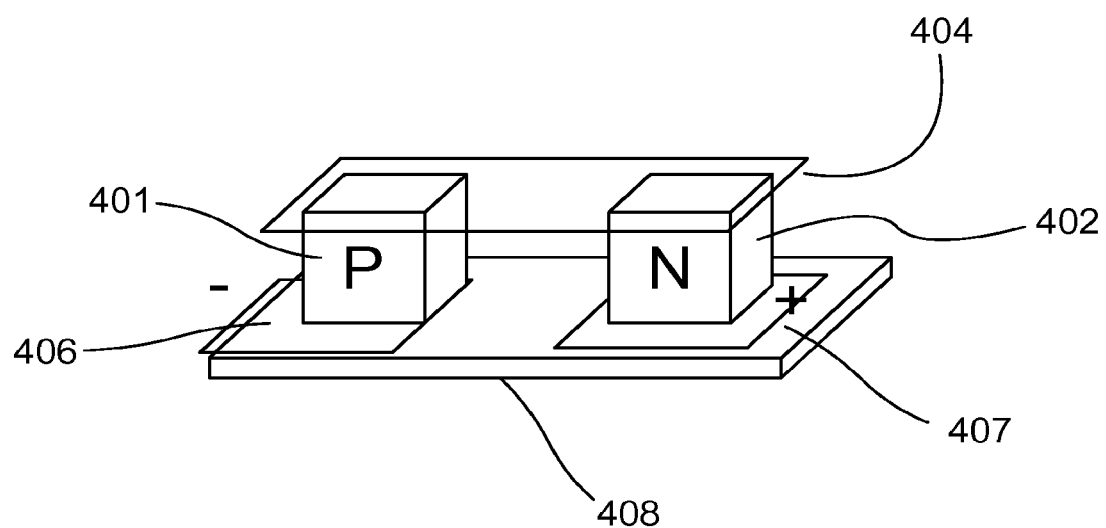
FIG. 9 is a schematic illustration of an individual thermoelectric cooling unit.

FIG. 9 schematically illustrates a thermoelectric or Peltier cooling unit, a multiplicity of which can be arranged to form a Peltier cooling module. The thermoelectric unit comprises a p-type semiconductor 401 (such as for example Lead Telluride) electrically in series with an n-type semiconductor 402 (such as for example Bismuth Telluride) and connected by a metallic connection 404. At the same time, the semiconductors 401 and 402 are thermally connected in parallel. The disjoint ends of the p-type semiconductor and the n-type semiconductor are connected to metallic terminal electrodes 406 and 407 respectively with negative and positive electric polarities or voltages respectively, and the electrodes 406 and 407 abut a ceramic cover 408. When a voltage is applied to the terminal electrodes (so that terminal 406 is at a negative electric potential relative to terminal 407), a current flows from the n-type semiconductor 402 through the series connection 404 and through the p-type semiconductor 401. The respective charge carriers in each semiconductor move from the top to the bottom, and correspondingly there is a heat flux that transports heat from the top face 404 of the Peltier cooling unit to the bottom face 408. Correspondingly 404 is turned into the "cold" or lower temperature face and 408 into the "hot" or higher temperature face of the Peltier cooling unit.

Figure 10:
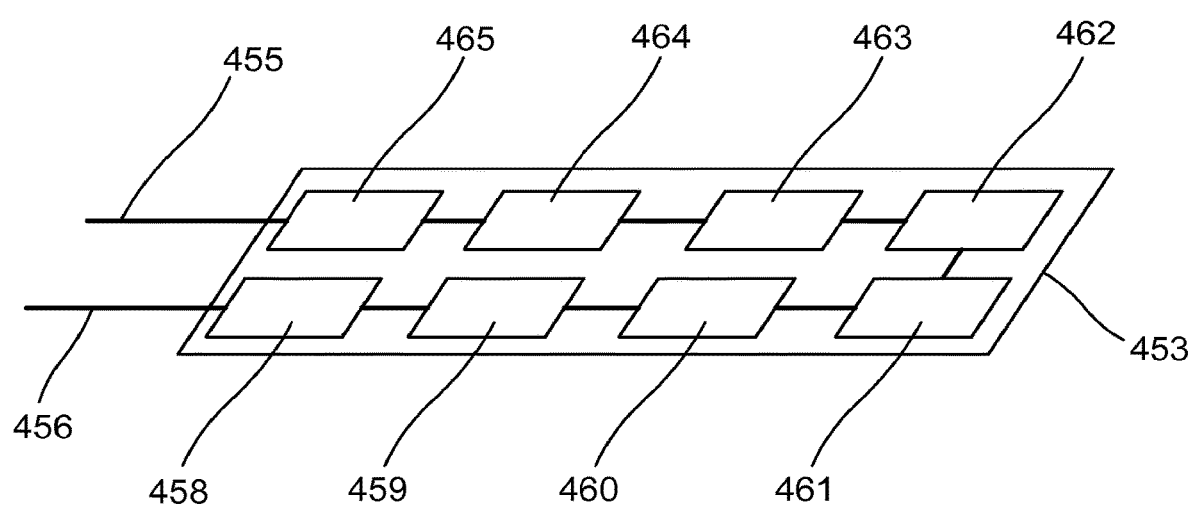
FIG. 10 is a schematic illustration of a thermoelectric cooling module according to an embodiment incorporating a multiplicity of thermoelectric cooling units.

FIG. 10 schematically depicts a chain of Peltier cooling units connected to form a thermoelectric cooling module. In this example, the module 453 comprises Peltier cooling units 458, 459, 460, 461, 462, 463, 464 and 465 connected in a chain so as to spread approximately uniformly over an area and such that all the units have for example a "hot side" on the bottom and a "cold" side on the top. An appropriate voltage can be applied across the end terminal leads 455 and 456 in order to drive a heat flux between the top and bottom sides and maintain a cold surface.

Thermoelectric heat pump modules are commercially available, for example from sources such as TE Technology, Inc. of Traverse City, Mich., USA and appropriate configurations convenient for the electrode clamp devices according to an embodiment can be arrived at by those skilled in the art.

Figure 11:
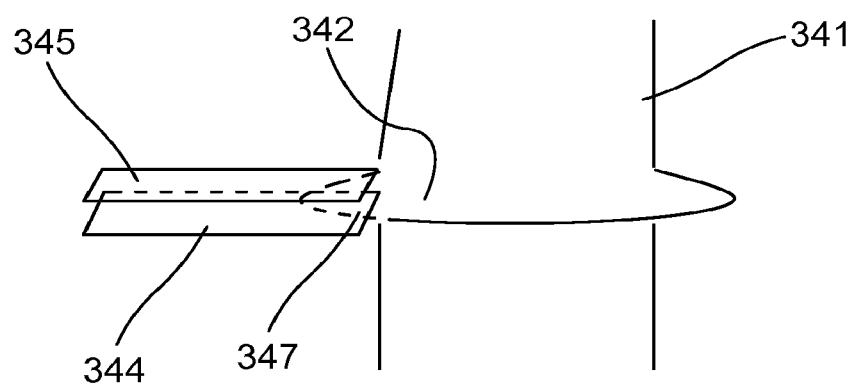
FIG. 11 is a schematic illustration of electrode clamp device placement geometry in relation to patient anatomy, according to an embodiment.
Figure 12:
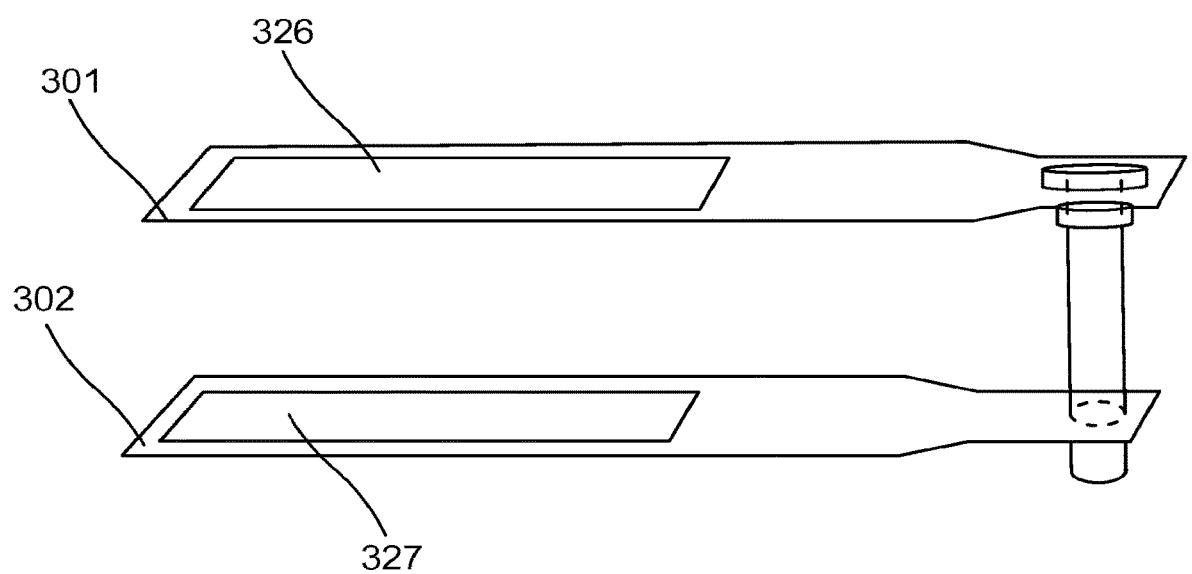
FIG. 12 is a schematic illustration of an electrode clamp device according to an embodiment showing electrode heads with large aspect ratio.
Figure 13:
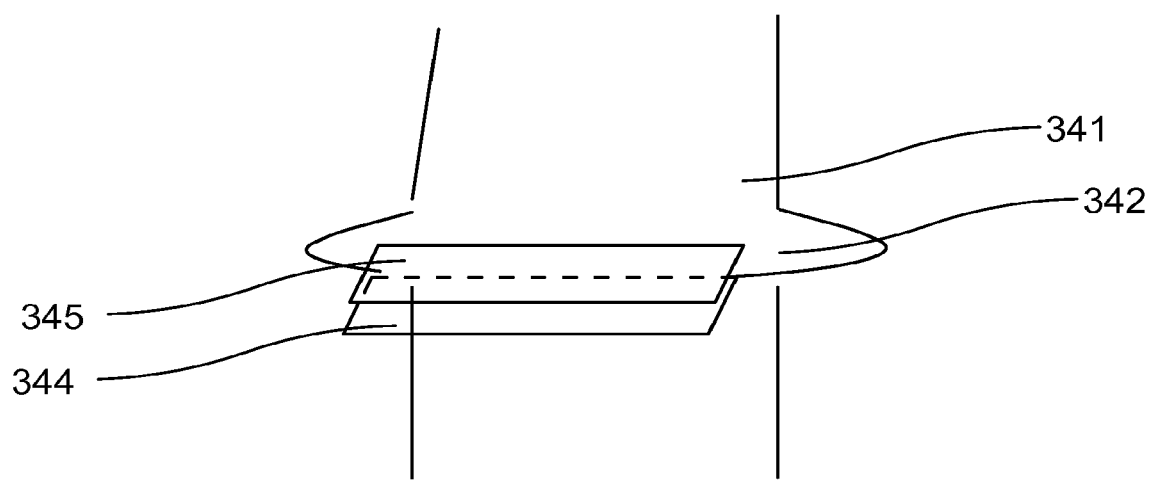
FIG. 13 is a schematic illustration of electrode clamps according to an embodiment with large aspect ratio electrode heads showing overall placement geometry in relation to patient anatomy.

FIG. 11 schematically illustrates one geometry of use of the electrode clamp device, wherein a portion 347 of skin and adipose tissue 342 disposed around a patient anatomy 341 is clamped between electrode arms 344 and 345 for electroporation ablation. FIG. 12 is an illustration of an electrode clamp device with electrode arms 301 and 302 wherein their respective electrode heads 326 and 327 are longitudinally disposed and have large aspect ratios, as shown schematically therein. As shown in the geometry depicted schematically in FIG. 13, such an arrangement could be used to clamp, in a lengthwise disposition, a portion of skin and adipose tissue 342 disposed around a patient anatomy 341 between electrode arms 344 and 345 for electroporation ablation.

In some embodiments, the time for which a cold temperature is maintained at the patient contacting surface of the electrode head is monitored and varied, so that the cooling control is applied in time in a pulse-like format. This is done in order to maintain a surface layer of tissue at a suitably low or cold temperature, while ensuring that deeper regions of tissue undergo no more than marginal cooling. The thermal diffusivity D of skin tissue is known to be in the range of 0.11 mm$^2$/s. From standard heat diffusion theory, in a time T the depth x to which a temperature change applied at the surface is propagated is given (in two dimensions) by x~$\sqrt{2DT}$; in 20 seconds of cooling, we have x~2 mm, about the thickness of skin tissue. In one mode of operation of the system according to an embodiment, the cooling of the electrodes is performed in discrete time intervals in the range of 10 seconds to 40 seconds, followed by a pulse train application, the entire duration of the pulse train being in the range of less than about 8 seconds. Thus, the application of cooling could also be performed in pulses. The next ablation in the same tissue region is performed, if necessary, after another cooling pulse is applied over a discrete time interval, and so on. In some embodiments, a heating pulse could follow a cooling pulse in order to ensure that the temperature in the interior of the tissue does not fall below a threshold value. Such a heating pulse can be applied when a thermoelectric or Peltier heat pump is used simply by reversing the polarity of the (voltage) control signal to the heat pump, and the heating pulse could have a duration in the range between 2 and 30 seconds.

Figure 14:
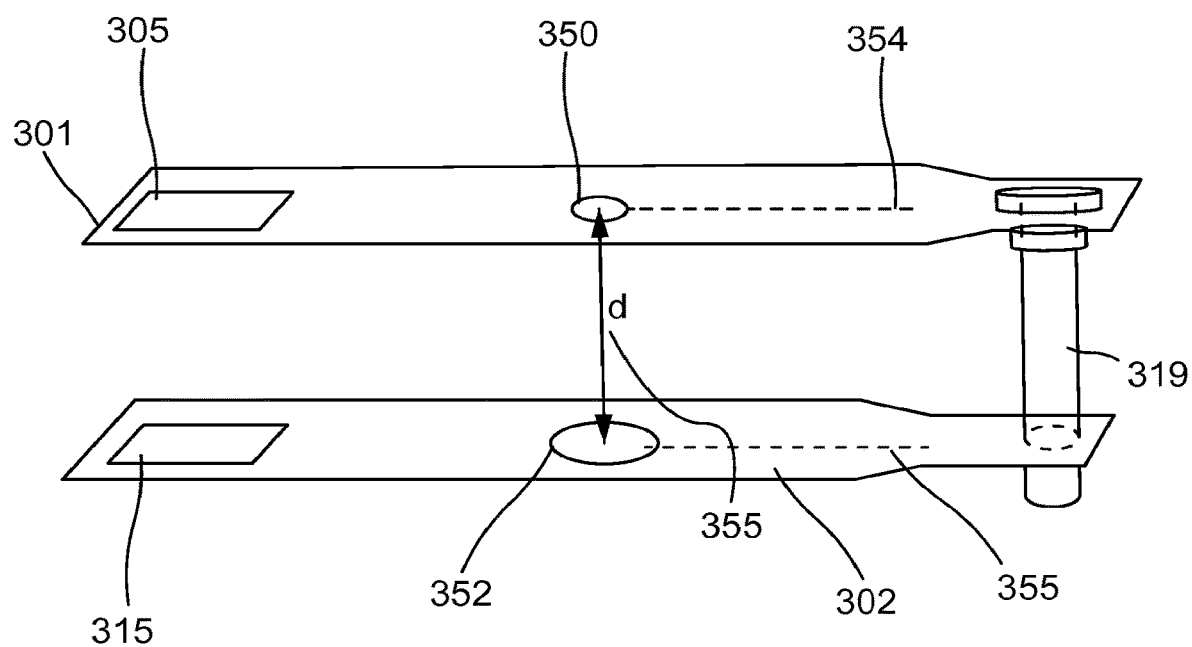
FIG. 14 is a schematic illustration of an electrode clamp device for irreversible electroporation according to an embodiment, further incorporating means for sensing separation or distance in the form of suitable sensors mounted away from the electrode heads.

FIG. 14 illustrates schematically one embodiment, where the electrode clamp device with electrode arms 301 and 302 with respective electrode heads 305 and 35 further has a sensor for measuring separation distance, in the form of an electromagnetic transmitter 352 on electrode arm 302 and an electromagnetic receiver coil 350 on electrode arm 301. Leads 354 and 355 respectively connect to receiver 350 and transmitter 352. Based on the signal intensity received by the receiver 350, the distance of separation d indicated by 355 in the FIG. can be measured. For example, if the axes and centers of the transmitter and receiver sensors are aligned, and a current I flows through the transmitter (of radius a), the magnetic field B at the center of the receiver is given by $$B = \frac{\mu_0 I a^2}{2(d^2 + a^2)^{3/2}} \quad (1)$$

where $\mu_0$ is the magnetic permeability of free space. If the current in the transmitter is sinusoidal with circular frequency $\omega$, the time varying magnetic field induces a voltage in the receiver given to a good approximation by $$V = \omega \frac{\mu_0 I a^2 A}{2(d^2 + a^2)^{3/2}} \quad (2)$$

Where A is the area of the receiver. Thus by measuring the induced voltage V, the separation distance d can be determined.

Figure 15:
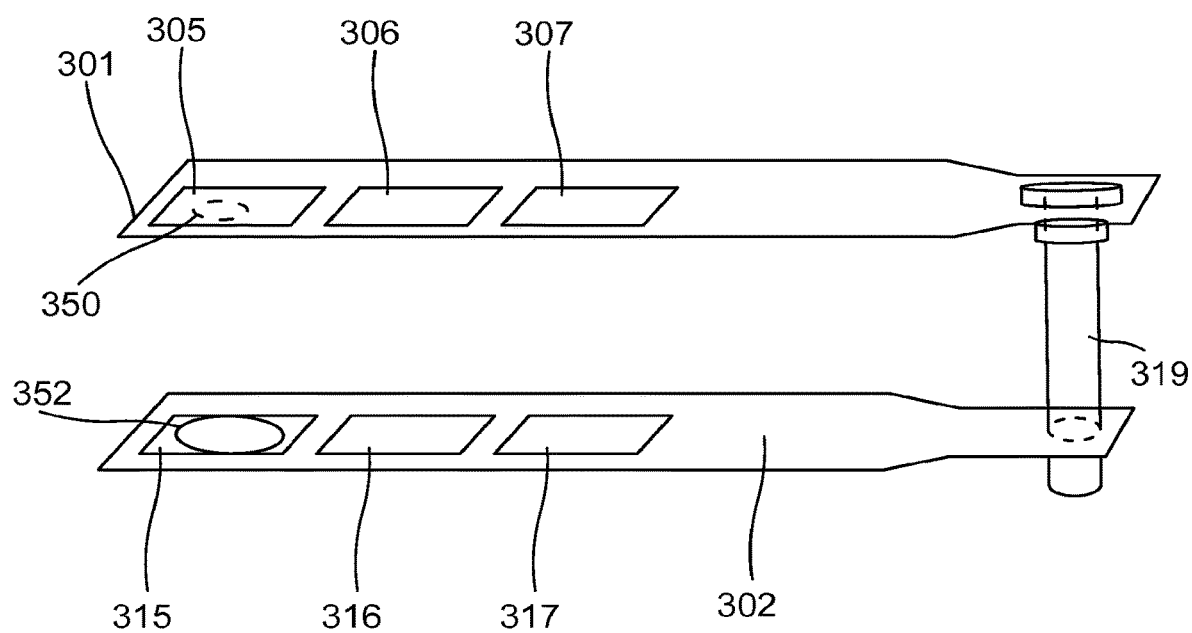
FIG. 15 is a schematic illustration of an electrode clamp device for irreversible electroporation according to an embodiment, further incorporating means for sensing separation or distance in the form of suitable sensors mounted on the electrode heads.

While in FIG. 14 the transmitter and receiver sensors for distance determination were located at a separation away from the electrode heads to mitigate electromagnetic interference with the metallic electrodes, in an alternate embodiment, the transmitter and receiver sensors could be integrated within an electrode head, as shown schematically in FIG. 15. In FIG. 15, the transmitter 352 is incorporated in electrode head 315 of lower electrode arm 302, while receiver sensor 350 is incorporated in electrode head 305 of upper electrode arm 301. Also shown are other electrode heads 306, 307, 316 and 317. With this arrangement, the induced voltage at the receiver is calibrated over a range of separations of the electrode arms, in effect generating a lookup table. The electromagnetic interference of the electrode heads is implicitly accounted for by this calibration process; subsequently, given a measured induced voltage at the receiver, the separation distance can be determined from the calibration data.

While the foregoing described one method of separation distance determination based on an electromagnetic scheme purely for illustrative and exemplary purposes, it should be apparent that a variety of other methods are available for this purpose such as for example schemes based on the use of ultrasound transmitters and receivers or infrared transmitters and receivers. Based on the teachings herein, those skilled in the art could arrive at an implementation that may be convenient for a specific application.

With a separation distance between electrode heads thus determined, the applied voltage to the electrode heads is then correspondingly determined based on a desired irreversible electroporation threshold value. For example, if the distance between electrode heads is measured to be 4 cm, and the desired irreversible electroporation threshold value is an electric field of 800 Volts/cm, it is clear that a voltage of at least 3.2 kV (desired electric field times distance) needs to be applied between the electrodes in order to meet or exceed the threshold value for irreversible electroporation.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices.

Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

While various specific examples and embodiments of systems and tools for selective tissue ablation with irreversible electroporation were described in the foregoing for illustrative and exemplary purposes, it should be clear that a wide variety of variations and alternate embodiments could be conceived or constructed by those skilled in the art based on the teachings according to an embodiment. While specific methods of control and DC voltage application from a generator capable of selective excitation of sets of electrodes were disclosed together with temperature control, persons skilled in the art would recognize that any of a wide variety of other control or user input methods can be implemented without departing from the scope according to an embodiment. Likewise, while the foregoing described a range of specific tools or devices for more effective and selective DC voltage application for irreversible electroporation through an externally applied electrode clamp device, other device constructions or variations could be implemented by one skilled in the art by employing the principles and teachings disclosed herein without departing from the scope according to an embodiment, in the treatment of excessive adipose tissue, tumor ablation, or a variety of other medical applications.

Furthermore, while the present disclosure describes specific embodiments and tools involving the use of temperature to selectively ablate tissue by taking advantage of the temperature-dependence of the threshold of irreversible electroporation and the application of specific cooling methodologies for exemplary purposes, it should be clear to one skilled in the art that a variety of methods and devices for fluid pumping and control, for tissue or electrode cooling, or even for tissue heating through the delivery of focused kinetic energy or electromagnetic radiation could be implemented utilizing the methods and principles taught herein without departing from the scope according to an embodiment.

Accordingly, while many variations of methods and tools disclosed here can be constructed, the scope according to an embodiment is limited only by the appended claims.

The invention claimed is:
1. An apparatus, comprising:
a clamp including a first arm and a second arm, the first arm and the second arm configured to exert opposing forces to maintain a target tissue between the first arm and the second arm;
a first electrode head coupled to the first arm, the first electrode head including a first electrically insulating contact surface, a first electrode enclosed within the first electrode head such that the first electrode is insulated from contacting the target tissue, and a first cooling unit, the first electrically insulating contact surface configured to contact a first portion of the target tissue, the first cooling unit configured to maintain the first portion of the target tissue at a first target temperature; and a second electrode head coupled to the second arm, the second electrode head including a second electrically insulating contact surface, a second electrode enclosed within the second electrode head such that the second electrode is insulated from contacting the target tissue, and a second cooling unit, the second electrically insulating contact surface configured to contact a second portion of the target tissue, the second cooling unit configured to maintain the second portion of the target tissue at a second target temperature, the first electrode and the second electrode collectively configured to generate a pulsed electric field to ablate the target tissue.

2. The apparatus of claim 1, wherein at least one of the first target temperature or the second target temperature is about 55 degrees Fahrenheit or less.

3. The apparatus of claim 1, wherein at least one of the first cooling unit or the second cooling unit is any one of a cooling coil, a thermo-electric cooler or a heat pump.

4. The apparatus of claim 1, wherein the first electrode head includes a sensor configured to measure a temperature of the first portion of the target tissue.

5. The apparatus of claim 1, wherein the clamp is configured to maintain a distance between the first electrode head and the second electrode head within a predetermined range.

6. The apparatus of claim 1, wherein the clamp is includes an adjustment member configured to adjust a distance between the first electrode head and the second electrode head.

7. The apparatus of claim 1, further comprising:
a sensor configured to produce a distance signal associated with a distance between the first electrode head and the second electrode head.

8. The apparatus of claim 7, wherein the sensor is any one of an electromagnetic sensor or an ultrasound sensor.

9. The apparatus of claim 1, wherein the first electrode head includes a temperature sensor configured to measure a temperature of the first portion of the target tissue, the apparatus further comprising:
a sensor configured to produce a distance signal associated with a distance between the first electrode head and the second electrode head.

10. The apparatus of claim 1, wherein the first electrode head includes a body supported by the first arm, the body and the first electrically insulating contact surface collectively enclosing the first electrode such that the first electrode is insulated from contacting the target tissue.

11. An apparatus, comprising:
a clamp including a first arm and a second arm, the first arm and the second arm defining a volume to receive a target tissue;
a first electrode head coupled to the first arm, the first electrode head including:
a first electrically insulating contact surface configured to contact a first portion of the target tissue;
a first electrode including a side facing the volume for receiving the target tissue, the first electrically insulating contact surface covering the side of the first electrode to prevent contact between the first electrode and the target tissue; and
a first cooling unit configured to cool the first portion of the target tissue to a first temperature below a body temperature; and
a second electrode head coupled to the second arm, the second electrode head including:
a second electrically insulating contact surface configured to contact a second portion of the target tissue;
a second electrode including a side facing the volume for receiving the target tissue, the second electrically insulating contact surface covering the side of the second electrode to prevent contact between the second electrode and the target tissue; and
a second cooling unit configured to cool the second portion of the target tissue to a second temperature below the body temperature,
the first electrode and the second electrode collectively configured to generate a pulsed electric field to ablate the target tissue.

12. The apparatus of claim 11, wherein the first temperature is the same as the second temperature.

13. The apparatus of claim 11, wherein at least one of the first cooling unit or the second cooling unit is any one of a cooling coil, a thermo-electric cooler or a heat pump.

14. A system, comprising:
a signal generator configured to generate a pulsed voltage waveform for causing irreversible electroporation of target tissue; and
a clamp operatively coupled to the signal generator, the clamp including:
a first arm and a second arm, the first arm and the second arm configured to exert opposing forces to maintain the target tissue between the first arm and the second arm;
a first electrode head coupled to the first arm, the first electrode head including:
a first electrically insulating contact surface configured to contact a first portion of the target tissue;
a first electrode; and
a first cooling unit configured to maintain the first portion of the target tissue at a first target temperature; and
a second electrode head coupled to the second arm, the second electrode head including:
a second electrically insulating contact surface configured to contact a second portion of the target tissue;
a second electrode; and
a second cooling unit configured to maintain the second portion of the target tissue at a second target temperature,
the first and second electrodes, in response to receiving an output based on the pulsed voltage waveform, configured to generate a pulsed electric field that causes the irreversible electroporation of the target tissue.

15. The system of claim 14, wherein the pulsed voltage waveform has an amplitude in the range between about 0.5 kV to about 60 kV.

16. The system of claim 14, wherein the pulsed voltage waveform has an amplitude in the range between about 1 kV to about 10 kV.

17. The system of claim 14, wherein at least one of the first cooling unit or the second cooling unit is any one of a cooling coil, a thermo-electric cooler or a heat pump.

18. The system of claim 14, wherein at least one of the first target temperature or the second target temperature is about 55 degrees Fahrenheit or less.

19. The system of claim 14, further comprising:
a sensor configured to produce a distance signal associated with a distance between the first electrode head and the second electrode head.

20. The system of claim 14, wherein the first electrically insulating contact surface and the second electrically insulating contact surface are configured to prevent direct current transfer between the first electrode and the second electrode.

* * * * *